United States Patent

Freese et al.

(10) Patent No.: US 9,459,244 B2
(45) Date of Patent: Oct. 4, 2016

(54) IMPLEMENTATION CONCEPTS AND RELATED METHODS FOR OPTICAL COMPUTING DEVICES

(71) Applicant: Halliburton Energy Services, Inc., Houston, TX (US)

(72) Inventors: Robert P. Freese, Pittsboro, NC (US); Christopher M. Jones, Houston, TX (US); Michael T. Pelletier, Houston, TX (US); David L. Perkins, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/783,349

(22) PCT Filed: Jun. 20, 2013

(86) PCT No.: PCT/US2013/046840
§ 371 (c)(1),
(2) Date: Oct. 8, 2015

(87) PCT Pub. No.: WO2015/105474
PCT Pub. Date: Jul. 16, 2015

(65) Prior Publication Data
US 2016/0054285 A1    Feb. 25, 2016

(51) Int. Cl.
| | | |
|---|---|---|
| *G01N 21/00* | (2006.01) |
| *G01N 33/28* | (2006.01) |
| *G01J 3/40* | (2006.01) |
| *G01N 21/85* | (2006.01) |
| *E21B 47/10* | (2012.01) |
| *G01N 21/25* | (2006.01) |
| *G01N 21/27* | (2006.01) |
| *G01N 21/64* | (2006.01) |

(52) U.S. Cl.
CPC ......... *G01N 33/2823* (2013.01); *E21B 47/102* (2013.01); *G01J 3/40* (2013.01); *G01N 21/255* (2013.01); *G01N 21/27* (2013.01); *G01N 21/8507* (2013.01); *G01N 21/643* (2013.01); *G01N 21/645* (2013.01); *G01N 2021/8514* (2013.01); *G01N 2021/8528* (2013.01)

(58) Field of Classification Search
CPC .. G01N 21/31; G01N 21/35; G01N 15/0205; G01N 33/383; G01N 21/85; G06E 3/001; G06E 1/00; E21B 43/25; E21B 43/16; E21B 47/10; C04B 40/0032; C04B 28/02
USPC .................... 356/432, 70, 335, 337, 477, 73
See application file for complete search history.

(56) References Cited

U.S. PATENT DOCUMENTS

| | | |
|---|---|---|
| 2004/0017569 A1 | 1/2004 | Payne |
| 2008/0276687 A1 | 11/2008 | Myrick et al. |
| 2010/0245096 A1 | 9/2010 | Jones et al. |

(Continued)

OTHER PUBLICATIONS

International Search Report and The Written Opinion of the International Searching Authority, or the Declaration, Aug. 27, 2015, PCT/US2013/046840, 12 pages, ISA/KR.

*Primary Examiner* — Tarifur Chowdhury
*Assistant Examiner* — Isiaka Akanbi
(74) *Attorney, Agent, or Firm* — Haynes and Boone, LLP

(57) ABSTRACT

Various implementations of optical computing devices are described herein which include a "tuning fork" probe, "spark plug" probe, "grooved tubular" and "modular" type implementation.

77 Claims, 6 Drawing Sheets

(56) References Cited

U.S. PATENT DOCUMENTS

| | | |
|---|---|---|
| 2012/0242993 A1 | 9/2012 | Schick et al. |
| 2013/0032334 A1* | 2/2013 | Freese .................... E21B 43/26 166/250.01 |
| 2013/0032545 A1* | 2/2013 | Freese .................... C02F 1/008 210/739 |
| 2013/0032736 A1 | 2/2013 | Tunheim et al. |
| 2013/0034842 A1* | 2/2013 | Tunheim ................ G01N 21/85 435/3 |
| 2014/0080224 A1* | 3/2014 | Tunheim ................ G01N 21/17 436/164 |
| 2014/0352953 A1* | 12/2014 | Gao ...................... E21B 43/128 166/250.15 |

* cited by examiner

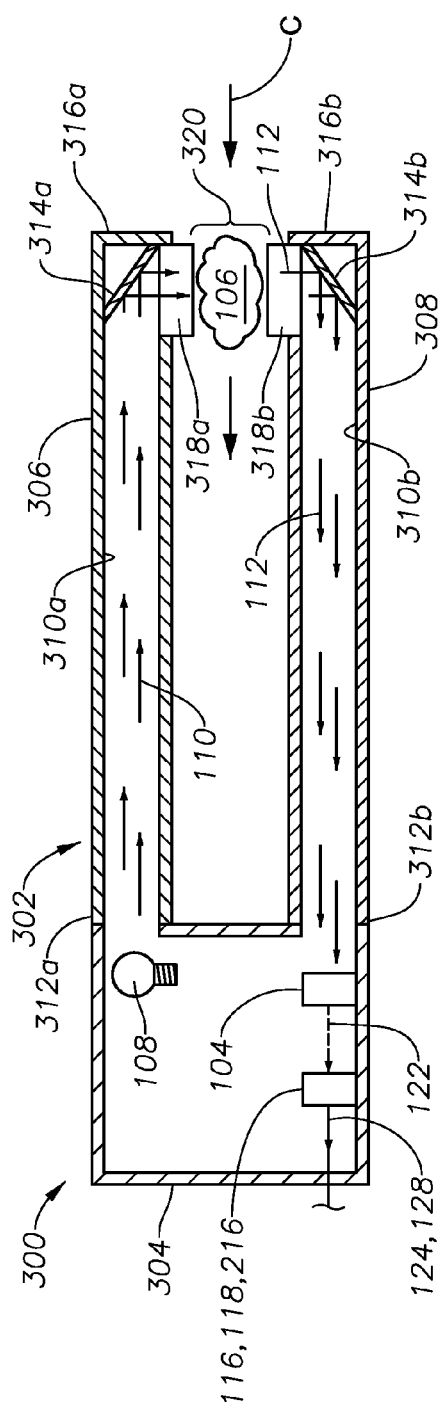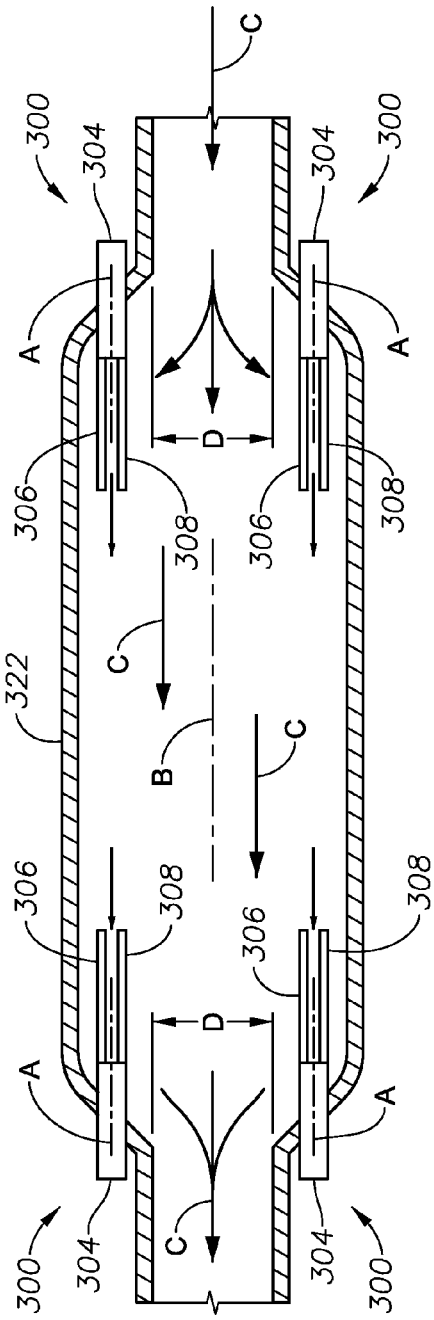
FIG. 3A
FIG. 3B

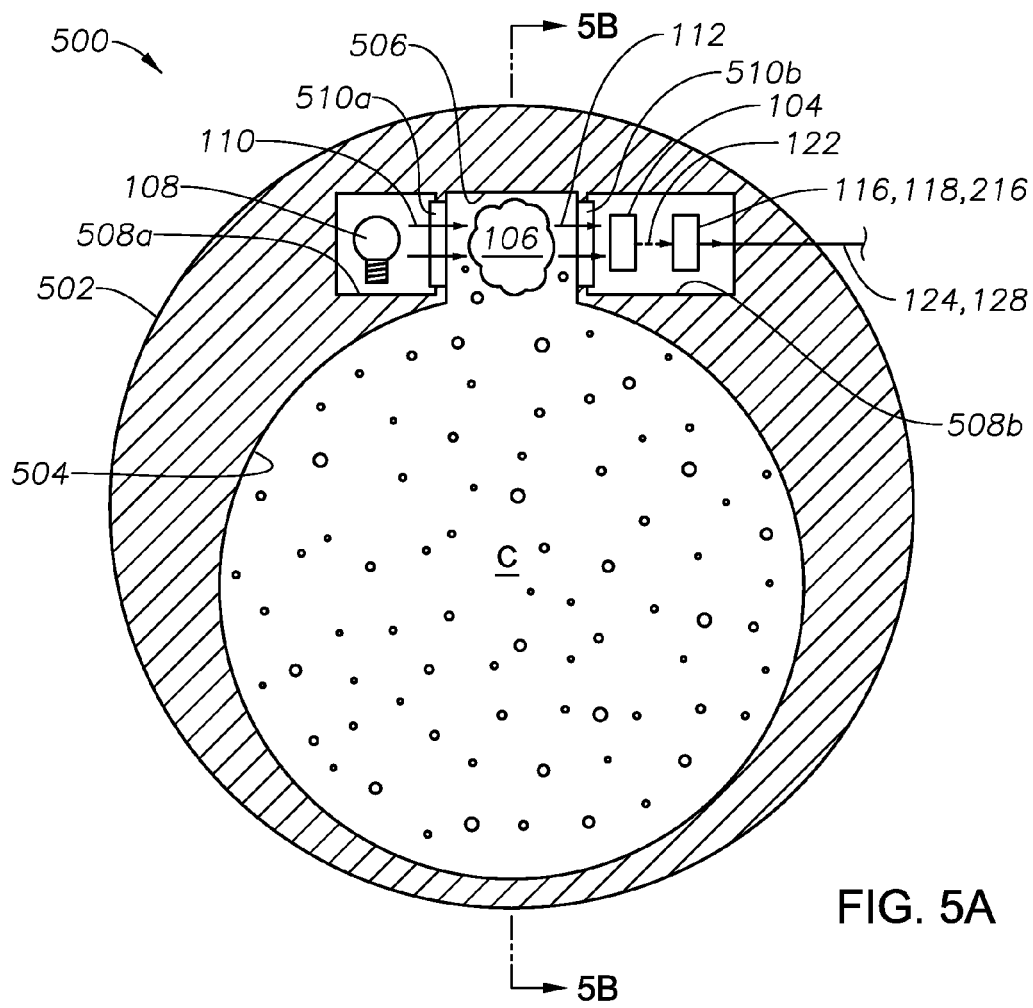
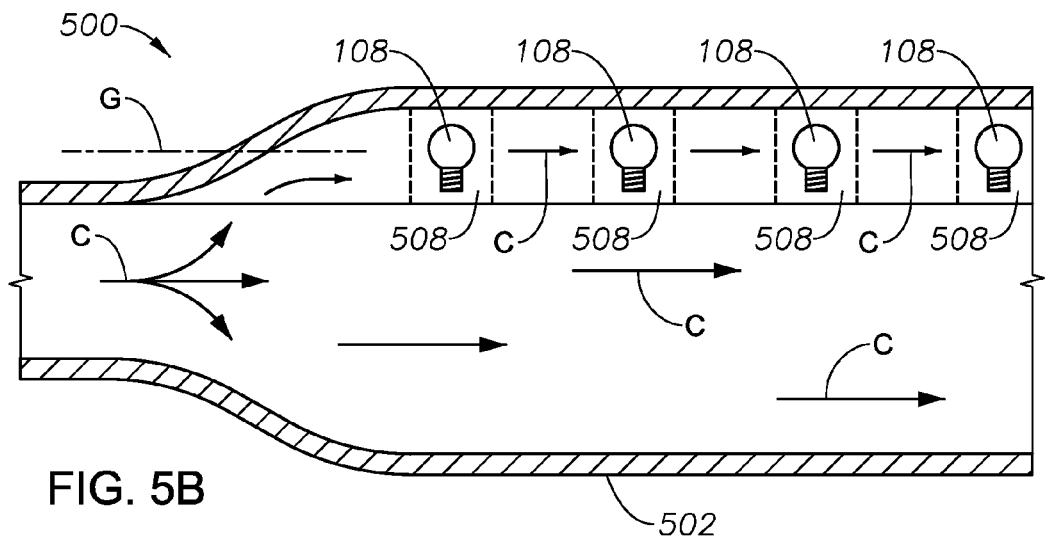

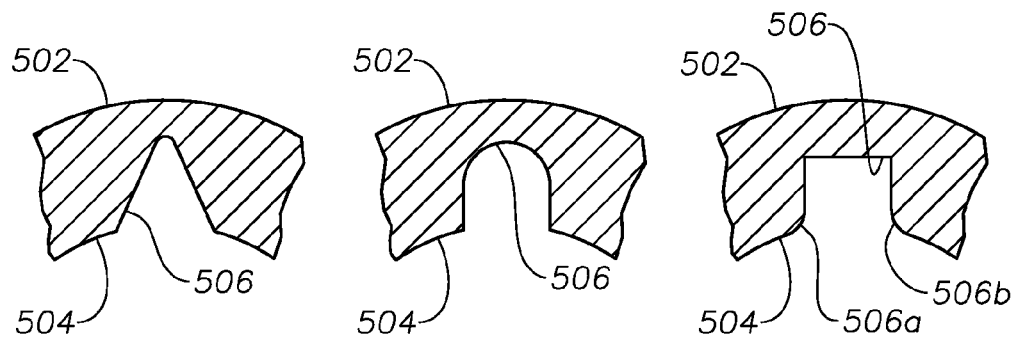
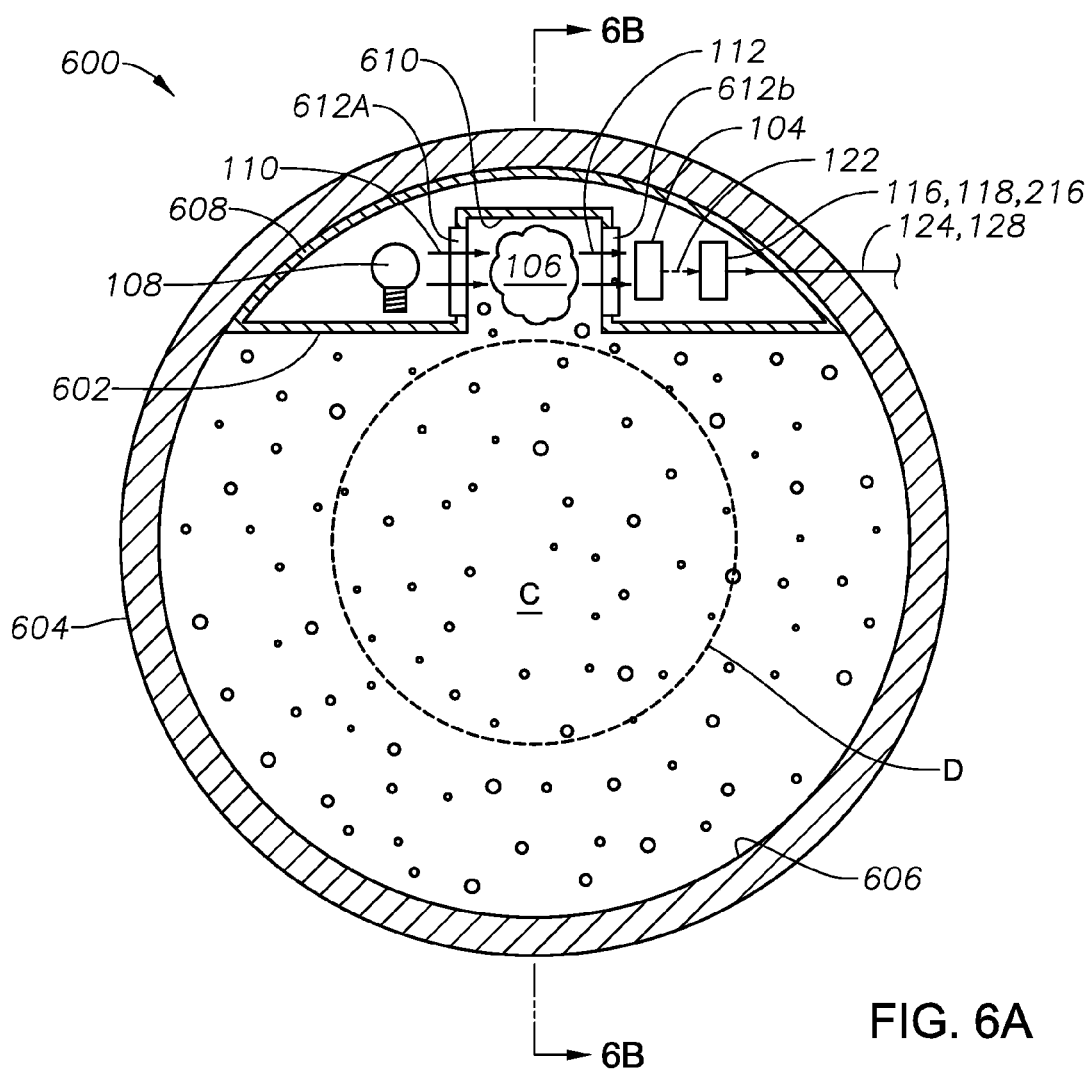

IMPLEMENTATION CONCEPTS AND RELATED METHODS FOR OPTICAL COMPUTING DEVICES

The present application is a U.S. National Stage patent application of International Patent Application No. PCT/US2013/046840, filed on Jun. 20, 2013, the benefit of which is claimed and the disclosure of which is incorporated herein by reference in its entirety.

FIELD OF THE INVENTION

The present invention relates generally to optical computing devices and, more specifically, to various methods by which to embody, or implement, such optical computing devices.

BACKGROUND

In recent years, optical computing techniques have been developed for applications in the Oil and Gas Industry in the form of optical sensors on downhole or surface equipment to evaluate a variety of fluid properties. An optical computing device is a device configured to receive an input of electromagnetic radiation from a substance or sample of the substance and produce an output of electromagnetic radiation from a processing element, also referred to as an optical element. The optical element may be, for example, a narrow band optical element or an Integrated Computational Element ("ICE") (also known as a Multivariate Optical Element ("MOE").

Fundamentally, optical computing devices utilize optical elements to perform calculations, as opposed to the hardwired circuits of conventional electronic processors. When light from a light source interacts with a substance, unique physical and chemical information about the substance is encoded in the electromagnetic radiation that is reflected from, transmitted through, or radiated from the sample. Thus, the optical computing device, through use of the ICE core and one or more detectors, is capable of extracting the information of one or multiple characteristics/properties or analytes within a substance and converting that information into a detectable output signal reflecting the overall properties of a sample. Such characteristics may include, for example, the presence of certain elements, compositions, fluid phases, etc. existing within the substance.

Therefore, a need has arisen in the industry to develop ways in which to temporarily or permanently place optical computing devices in downhole tubing or piping. Such pipes and tubes are used for the production of reservoir fluids and can be in place for many years. As the well is produced, it is desired to know the composition of the fluids, as this knowledge is used in part to make decisions how to treat the fluids once they reach surface. However, there are considerations that dictate the configuration of sensors used in permanent placement applications. For example, the sensor needs to be robust and require little power, to allow it to be in place for many years. The sensors also need to be of sufficient size such that other tools and systems can be conveyed past the installed sensor along the tubing/pipe. Additionally, the sensors should minimally affect the flow of fluid in the tube. If the sensor affects the flow, there can be variations in the volumetric flow rate or pressure. These effects may lead to changes in the fluids composition. For example, solids entrained in the fluid may fall out and build up in low volumetric flow areas leading to eventual blockage. Alternatively, changes in pressure can cause dissolved gases to evolve from the fluid leading to inaccurate estimations of the fluids composition.

Moreover, traditional spectrometer instruments simply are not stable enough to withstand downhole conditions. Filter photometers are reasonably stable, but do not have the sensitivity to measure analytes of interest in complex oils. Additionally, many instruments cannot measure across large concentration ranges. For example, the water cut application requires a 0 to 100% water (or oil) coverage, and traditional instruments generally only detect a small fraction of this range . . . e.g. 0 to 10% or 70 to 80%. Finally, the sensors need to be low cost in order to place them along each collection tubular. So, for example, a single producing well might use up to 1,000 or more single sensors. If these cost ~½ Million each as do some traditional sensors, this is clearly a large barrier to overcome.

Accordingly, the present invention meets these and other needs in the art through provision of cost-effective, robust, stabile, compact and power efficient implementations for optical computing devices as described herein.

BRIEF DESCRIPTION OF THE DRAWINGS

FIG. 3A illustrates a sectional block diagram of a tuning fork probe implementation of an optical computing device, according to certain exemplary embodiments of the present invention;

FIG. 3B illustrates a sectional view of a tubular having a plurality of tuning fork probes positioned radially around the body of a tubular, according to certain exemplary embodiments of the present invention;

FIG. 5A illustrates a sectional block diagram of a grooved tubular implementation of an optical computing device, according to certain exemplary embodiments of the present invention;

FIG. 5B illustrates a sectional view of the length of the grooved tubular of FIG. 5A;

FIGS. 5C and 5D are sectional simplified views of the grooved tubular of FIG. 5A intended to illustrate alternative profile shapes for the optical groove;

FIG. 5E is yet another sectional simplified view of the optical groove of FIG. 5A intended to illustrate how certain embodiments of the optical groove taper into the bore of the tubular; and FIGS. 6A and 6B illustrate a sectional block diagram of a module implementation and a sectional view along the length of the module implementation, respectively, of an optical computing device, according to certain exemplary embodiments of the present invention.

DESCRIPTION OF ILLUSTRATIVE EMBODIMENTS

Figure 1:
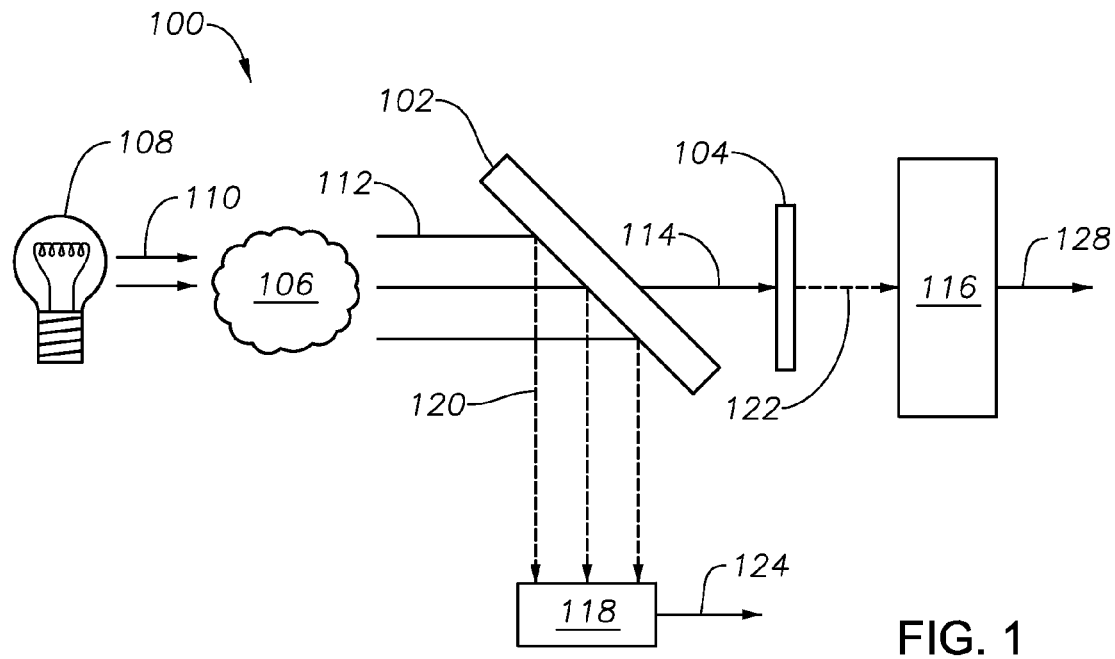
FIG. 1 is a block diagram of an exemplary architecture of an optical computing device employing a transmission mode design, which may be utilized in one or more of the optical computing devices of the present invention.

Illustrative embodiments and related methodologies of the present invention are described below as they might be employed in various methods by which to implement optical computing devices. In the interest of clarity, not all features of an actual implementation or methodology are described in this specification. Also, the "exemplary" embodiments described herein refer to examples of the present invention. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the invention will become apparent from consideration of the following description and drawings.

As described herein, exemplary embodiments of the present invention are directed to a "tuning fork" probe, "spark plug" probe, "grooved tubular" and "modular" type implementations for optical computing devices. Although described with reference to oil and gas-related implementations, the optical computing devices may be utilized in a variety of other applications in which it is desired to determine one or more characteristics of a sample. Other applications may include, for example, those as diverse as those associated with surface and undersea monitoring, satellite or drone surveillance, pipeline monitoring, or even sensors transiting a body cavity such as a digestive tract. Within those environments, the optical computing devices are utilized to detect/monitor various compounds or characteristics in order to monitor, in real time, various phenomena occurring within the environment.

As described herein, certain exemplary embodiments of the tuning fork probe implementation include an electromagnetic radiation source, optical element, detector and two rods which are inserted into a tubular body. A gap is formed between the rods through which a fluid sample may flow. As the fluid flows through the gap, electromagnetic radiation is transmitted through the rods and across the gap, whereby a characteristic of the fluid is determined. In certain embodiments, the electromagnetic radiation source, optical element and detector are housed outside the rods. Alternatively, one or more of the electromagnetic radiation source, optical element or detector may be positioned along the rods.

Certain exemplary embodiments of the spark plug probe implementation include a probe body that may be inserted into a tubular body. The probe body houses an electromagnetic source, optical element, detector and a flow channel through which a fluid sample may flow. The flow channel extends though the probe body along an axis that traverses an axis of the probe body. Additionally, the probe body may include a diverter to divert fluid traveling through the tubular to an inlet port of the flow channel. At least one characteristic of the fluid sample is determined it flows through the fluid channel.

Certain exemplary embodiments of the grooved tubular implementation include a tubular body having a bore therethrough, and an optical groove that extends along the bore in which a fluid sample is allowed to flow. Within the body of the tubular on either side of the optical groove are positioned an electromagnetic radiation source, optical element and a detector. As the fluid sample flows along the optical groove, electromagnetic radiation is emanated across the optical groove in a direction that traverses the axis of the optical groove. The optical element is positioned opposite the electromagnetic radiation source in order to receive the light (which has interacted with the fluid sample) and produce the output necessary to determine the desired characteristic of the fluid.

Certain exemplary embodiments of the modular implementation include a device housing which may be removably attached to a fluid-containing body. The device housing includes an optical groove positioned on its exterior surface such that fluid within the fluid-containing body is allowed to flow along the optical groove. Within the body of the device housing on either side of the optical groove are positioned an electromagnetic radiation source, optical element and a detector. As the fluid sample flows along the optical groove, electromagnetic radiation is emanated across the optical groove in a direction that traverses the axis of the optical groove. The optical element is positioned opposite the electromagnetic radiation source in order to receive the light (which has interacted with the fluid sample) and produce the output necessary to determine the desired characteristic of the fluid.

In view of the description provided below, these and other features and advantages of the various implementations described above will be readily understood by those ordinarily skilled in the art.

Again, although the optical computing devices described herein may be utilized in a variety of environments, the following description will focus on downhole well applications. FIG. 1 is a block diagram of an exemplary architecture of an optical computing device 100 employing a transmission mode design, which may be utilized in one or more of the optical computing devices of the present invention. An electromagnetic radiation source 108 may be configured to emit or otherwise generate electromagnetic radiation 110. As understood in the art, electromagnetic radiation source 108 may be any device capable of emitting or generating electromagnetic radiation. For example, electromagnetic radiation source 108 may be a light bulb, light emitting device, laser, blackbody, photonic crystal, or X-Ray source, natural luminescence, etc. In one embodiment, electromagnetic radiation 110 may be configured to optically interact with the sample 106 (wellbore fluid flowing through a wellbore or pipeline, for example) and generate sample-interacted light 112 directed to a beam splitter 102. Sample 106 may be any fluid (liquid or gas), solid substance or material such as, for example, downhole tool components, tubulars, rock formations, slurries, sands, muds, drill cuttings, concrete, other solid surfaces, etc. In other embodiments, however, sample 106 is a multiphase wellbore fluid (comprising oil, gas, water, solids, for example) consisting of a variety of fluid characteristics such as, for example, elemental corrosive by-products, elements generated by sample material loss, C1-C6 hydrocarbons, groupings of such elements, saline water, pH, total dissolved solids, sand content, $H_2S$, $CO_2$, asphaltenes, waxes, saturates, resins, or various production enhancement tracers or nanoparticles that have been added in neighboring wells to allow the tracking of fluid flow from one location to another.

Sample 106 may be provided to optical computing device 100 through a flow pipe or sample cell, for example, containing sample 106, whereby it is introduced to electromagnetic radiation 110. Alternatively, optical computing device 100 may utilize an optical configuration consisting of an internal reflectance element which analyzes the wellbore fluid as it flows thereby or which analyzes the surface of the sample (formation surface, for example). While FIG. 1 shows electromagnetic radiation 110 as passing through or incident upon the sample 106 to produce sample-interacted light 112 (i.e., transmission or fluorescent mode), it is also contemplated herein to reflect electromagnetic radiation 110 off of the sample 106 (i.e., reflectance mode), such as in the case of a sample 106 that is translucent, opaque, or solid, and equally generate the sample-interacted light 112.

After being illuminated with electromagnetic radiation 110, sample 106 containing an analyte of interest (a characteristic of the sample, for example) produces an output of electromagnetic radiation (sample-interacted light 112, for example). As previously described, sample-interacted light 112 also contains spectral information of the sample used to determine one or more characteristics of the fluid sample. Ultimately, a local or remote processor analyzes this spectral information to determine the desired characteristic of the sample 106. Although not specifically shown, one or more spectral elements may be employed in optical computing device 100 in order to restrict the optical wavelengths and/or bandwidths of the system and, thereby, eliminate unwanted electromagnetic radiation existing in wavelength regions that have no importance. As will be understood by those ordinarily skilled in the art having the benefit of this disclosure, such spectral elements can be located anywhere along the optical train, but are typically employed directly after the light source which provides the initial electromagnetic radiation.

Although not shown, optical computing device 100 may be coupled to a remote power supply (located on the surface or a power generator positioned downhole along the wellbore, for example), while in other embodiments optical computing device 100 comprises an on-board battery. Optical computing device 100 may also comprise a signal processor (not shown), communications module (not shown) and other circuitry necessary to achieve the objectives of the present invention, as will be understood by those ordinarily skilled in the art having the benefit of this disclosure. It will also be recognized that the software instructions necessary to carry out the objectives of the present invention may be stored within storage located on optical computing device 100 or loaded into that storage from a CD-ROM or other appropriate storage media via wired or wireless methods.

Alternatively, however, the processor may be located remotely from optical computing device 100. In such embodiments, a communications link provides a medium of communication between the processor and optical computing device 100. The communications link may be a wired link, such as, for example, a wireline or fiber optic cable. Alternatively, however, the link may be a wireless link, such as, for example, an electromagnetic device of suitable frequency, or other methods including acoustic communication and like devices.

In certain exemplary embodiments, the signal processor controls operation of optical computing device 100. Optical computing device 100 may also include a transmitter and receiver (transceiver, for example) (not shown) that allows bi-directional communication over a communications link in real-time. In certain exemplary embodiments, optical computing device 100 will transmit all or a portion of the sample characteristic data to a remote processor for further analysis. However, in other embodiments, such analysis is completely handled by optical computing device 100 and the resulting data is then transmitted remotely for storage or subsequent analysis. In either embodiment, the processor handling the computations may, for example, analyze the characteristic data, perform Equation of State ("EOS") or other optical analysis techniques, or perform simulations based upon the characteristic data, as will be readily understood by those ordinarily skilled in the art having the benefit of this disclosure.

Still referring to the exemplary embodiment of FIG. 1, beam splitter 102 is employed to split sample-interacted light 112 into a transmitted electromagnetic radiation 114 and a reflected electromagnetic radiation 120. Transmitted electromagnetic radiation 114 is then directed to one or more optical elements 104. Optical element 104 may be a variety of optical elements such as, for example, one or more narrow band optical filters or ICE cores arranged or otherwise used in series in order to determine the characteristics of sample 106. In those embodiments using ICE cores, the ICE core may be configured to be associated with a particular characteristic of sample 106 or may be designed to approximate or mimic the regression vector of the characteristic in a desired manner, as would be understood by those ordinarily skilled in the art having the benefit of this disclosure. Additionally, in an alternative embodiment, optical element 104 may function as both a beam splitter and computational processor, as will be understood by those same ordinarily skilled persons.

Further discussion of the design and operation of ICE cores can be found in, for example, U.S. Pat. No. 6,198,531, entitled "OPTICAL COMPUTATIONAL SYSTEM," issued to Myrick et al. on Mar. 6, 2001; U.S. Pat. No. 7,697,141, entitled "IN SITU OPTICAL COMPUTATION FLUID ANALYSIS SYSTEM AND METHOD," issued to Jones et al. on Apr. 13, 2010; and U.S. Pat. No. 8,049,881, entitled "OPTICAL ANALYSIS SYSTEM AND METHODS FOR OPERATING MULTIVARIATE OPTICAL ELEMENTS IN A NORMAL INCIDENCE ORIENTATION," issued to Myrick et al. on Nov. 1, 2011, each being owned by the Assignee of the present invention, Halliburton Energy Services, Inc., of Houston, Tex., the disclosure of each being hereby incorporated by reference in its entirety.

Nevertheless, transmitted electromagnetic radiation 114 then optically interacts with optical element 104 to produce optically interacted light 122. In this embodiment, optically interacted light 122, which is related to the characteristic or analyte of interest, is conveyed to detector 116 for analysis and quantification. Detector 116 may be any device capable of detecting electromagnetic radiation, and may be generally characterized as an optical transducer. For example, detector 116 may be, but is not limited to, a thermal detector such as a thermopile or photoacoustic detector, a semiconductor detector, a piezo-electric detector, charge coupled device detector, video or array detector, split detector, photon detector (such as a photomultiplier tube), photodiodes, local or distributed optical fibers, and/or combinations thereof, or the like, or other detectors known to those ordinarily skilled in the art. Detector 116 is further configured to produce an output signal 128 in the form of a voltage that corresponds to the characteristic of the sample 106. In at least one embodiment, output signal 128 produced by detector 116 and the characteristic concentration of the sample 106 may be directly proportional. In other embodiments, the relationship may be a polynomial function, an exponential function, and/or a logarithmic function.

Optical computing device 100 includes a second detector 118 arranged to receive and detect reflected electromagnetic radiation and output a normalizing signal 124. As understood in the art, reflected electromagnetic radiation 120 may include a variety of radiating deviations stemming from electromagnetic radiation source 108 such as, for example, intensity fluctuations in the electromagnetic radiation, interferent fluctuations (for example, dust or other interferents passing in front of the electromagnetic radiation source), combinations thereof, or the like. Thus, second detector 118 detects such radiating deviations as well. In an alternative embodiment, second detector 118 may be arranged to receive a portion of the sample-interacted light 112 instead of reflected electromagnetic radiation 120, and thereby compensate for electromagnetic radiating deviations stemming from the electromagnetic radiation source 108. In yet other embodiments, second detector 118 may be arranged to receive a portion of electromagnetic radiation 110 instead of reflected electromagnetic radiation 120, and thereby likewise compensate for electromagnetic radiating deviations stemming from the electromagnetic radiation source 108. Those ordinarily skilled in the art having the benefit of this disclosure will realize there are a variety of design alterations which may be utilized in conjunction with the present invention.

Although not shown in FIG. 1, in certain exemplary embodiments, detector 116 and second detector 118 may be communicably coupled to a signal processor (not shown) on-board optical computing device 100 such that normalizing signal 124 indicative of electromagnetic radiating deviations may be provided or otherwise conveyed thereto. The signal processor may then be configured to computationally combine normalizing signal 124 with output signal 128 to provide a more accurate determination of the characteristic of sample 106. However, in other embodiments that utilized only one detector, the signal processor would be coupled to the one detector. Nevertheless, in the embodiment of FIG. 1, for example, the signal processor computationally combines normalizing signal 124 with output signal 128 via principal component analysis techniques such as, for example, standard partial least squares which are available in most statistical analysis software packages (for example, XL Stat for MICROSOFT® EXCEL®; the UNSCRAMBLER® from CAMO Software and MATLAB® from MATHWORKS®), as will be understood by those ordinarily skilled in the art having the benefit of this disclosure. Thereafter, the resulting data is then transmitted to the processor for further operations.

Figure 2:
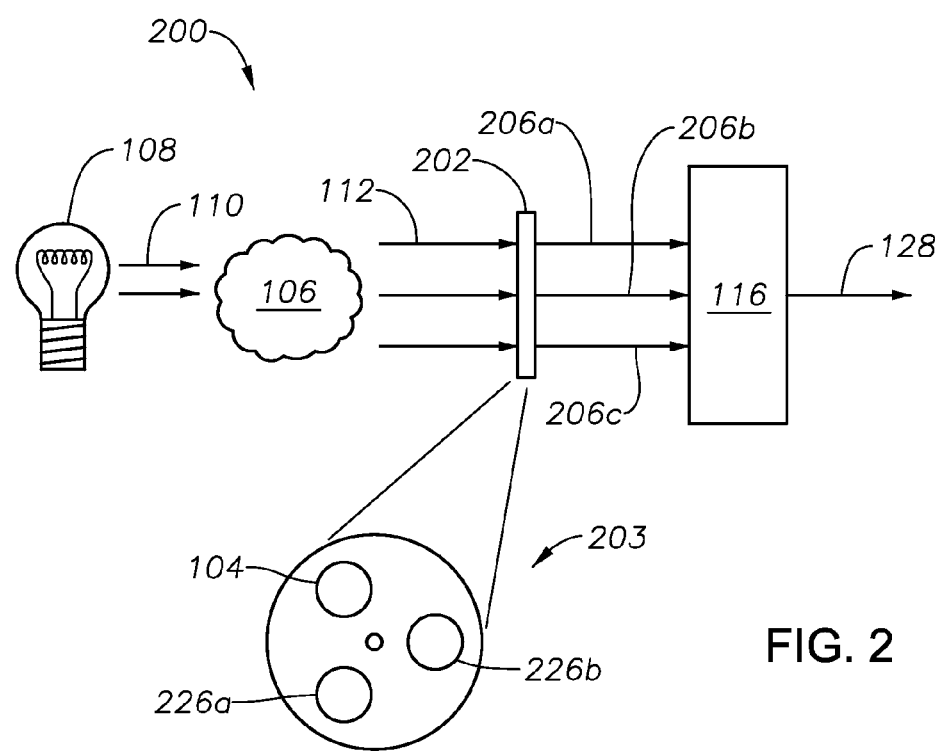
FIG. 2 is a block diagram of an exemplary architecture of an optical computing device employing a time domain mode design, which may be utilized in one or more of the optical computing devices of the present invention.

FIG. 2 is a block diagram of an exemplary architecture of an optical computing device 200 employing a time domain mode design, which may be utilized in one or more of the optical computing devices of the present invention. Optical computing device 200 is somewhat similar to optical computing device 100 described with reference to FIG. 1 and, therefore, may be best understood with reference thereto, where like numerals indicate like elements. Optical computing device 200 may include a movable assembly 202 having at least one optical element 104 and two additional optical elements 226a and 226b associated therewith. As illustrated, the movable assembly 202 may be characterized at least in one embodiment as a rotating disc 203, such as, for example, a chopper wheel, wherein optical elements 104, 226a and 226b are radially disposed for rotation therewith. FIG. 2 also illustrates corresponding frontal views of the moveable assembly 202, which is described in more detail below.

Those ordinarily skilled in the art having the benefit of this disclosure will readily recognize, however, that movable assembly 202 may be characterized as any type of movable assembly configured to sequentially align at least one detector with optically interacted light and/or one or more optical elements. Each optical element 104, 226a and 226b may be similar in construction to those as previously described herein, and configured to be either associated or disassociated with a particular characteristic of the sample 106. Although three optical elements are described, more or less optical elements may be employed along movable assembly 202 as desired.

In certain exemplary embodiments, rotating disc 203 may be rotated at a frequency of about 0.1 RPM to about 30,000 RPM. In operation, rotating disc 203 may rotate such that the individual optical elements 104, 226a and 226b may each be exposed to or otherwise optically interact with the sample-interacted light 112 for a distinct brief period of time. Upon optically interacting with the sample-interacted light 112, optical element 104 is configured to generate optically interacted light 206a (a first beam, for example), optical element 226a is configured to generate a second optically interacted light 206b (a second beam, for example) and optical element 226b is configured to generate a normalized electromagnetic radiation 206c (a normalization beam, for example). Detector 116 then receives each beam 206a-c and thereby generates a first, second and third output signal, respectively (output signal 128 comprises the first, second and third signals). Accordingly, a signal processor (not shown) communicatively coupled to detector 116 utilizes the output signal to computationally determine the sample characteristics.

Moreover, in certain exemplary embodiments, detector 116 may be configured to time multiplex beams 206a-c between the individually-detected beams. For example, optical element 104 may be configured to direct first beam 206a toward the detector 116 at a first time T1, optical element 226a may be configured to direct second beam 206b toward the detector 116 at a second time T2, and optical element 226b may be configured to direct third beam 206c toward detector 116 at a third time T3. Consequently, detector 116 receives at least three distinct beams of optically-interacted light which may be computationally combined by a signal processor (not shown) coupled to detector 116 in order to provide an output in the form of a voltage that corresponds to the characteristic of the sample, as previously described. In certain alternate embodiments, beams 206a-c may be averaged over an appropriate time domain (for example, about 1 millisecond to about 1 hour) to more accurately determine the characteristic of sample 106. As previously described, detector 116 is positioned to detect first, second and third beams 206a-c in order to produce output signal 128. In this embodiment, a signal processor (not shown) may be communicably coupled to detector 116 such that output signal 128 may be processed as desired to computationally determine the characteristic of sample 106.

Those ordinarily skilled in the art having the benefit of this disclosure realize the aforementioned optical computing devices are exemplary in nature, and that there are a variety of other optical configurations which may be utilized. These optical configurations not only include the reflection, absorption or transmission methods described herein, but can also involve scattering (Raleigh & Raman, for example) as well as emission (fluorescence, X-ray excitation, etc., for example). In addition, the optical computing devices may comprise a parallel processing configuration whereby the sample-interacted light is split into multiple beams. The multiple beams may then simultaneously go through corresponding ICE cores, whereby multiple characteristics and/or analytes of interest are simultaneously detected. The parallel processing configuration is particularly useful in those applications that require extremely low power or no moving parts. One such example of a parallel processing configuration is described in Patent Cooperation Treaty Application No. PCT/US2013/04680, filed on Jun. 20, 2013, entitled "OPTICAL COMPUTING DEVICE HAVING A REDUN- DANT POWER SOURCE AND OPTICAL TRAIN," which is hereby incorporated by reference in its entirety. In yet another alternate embodiment, various single or multiple ICE cores may be positioned in series in a single optical computing device. This embodiment is particularly useful if it is necessary to measure concentrations of the analytes in different locations (in each individual mixing pipe, for example). It is also sometimes helpful if each of the ICE cores use two substantially different light sources (UV and IR, for example) to cover the optical activity of all the characteristics or analytes of interest (i.e., some analytes might be only UV active, while others are IR active). Nevertheless, those ordinarily skilled in the art having the benefit of this disclosure will realize the choice of a specific optical configuration is mainly dependent upon the specific application and analytes of interest.

Now that exemplary fundamental architectures of optical computing devices have been described, various methods of which to implement those architectures will now be described. FIG. 3A illustrates a sectional block diagram of a tuning fork probe 300 implementation of optical computing device 100,200 according to certain exemplary embodiments of the present invention. Tuning fork probe 300 is a probe body 302 comprising a housing 304, first rod 306 and second rod 308. Housing 304 may be comprised of a high temperature/pressure resistant material such as, for example stainless steels and their alloys, titanium and other high strength metals, and even carbon fiber composites and sapphire or diamond structures, as understood in the art.

First rod 306 and second rod 308 are attached to housing 304 via any suitable method. First and second rods 306,308 comprise a bore 310a,310b, respectively, extending therethrough in which various electromagnetic radiations are communicated, as described in more detail below. First and second rods 306,308 may be comprised of a variety of materials such as, for example, aluminum, sapphire, glass, diamond, ZnSe, ZnS, Ge or Si. In this exemplary embodiment, electromagnetic radiation source 108, optical element 104 (ICE core, for example), detectors 216,218 and system electronics (not shown) are positioned within housing 304. Alternatively, however, electromagnetic radiation source 108, optical element 104, detectors 216,218 and system electronics (not shown) may be positioned along first and second rods, 306,308.

In this exemplary embodiment, electromagnetic radiation source 108 is positioned adjacent first end 312a of first rod 306 whereby it conveys electromagnetic radiation 110 through bore 310a and on to a first reflective element 314a (optical mirror, for example) positioned at the second end 316a. At first reflective element 314a, electromagnetic radiation 110 is reflected through a first window 318a, where it is then conveyed through gap 320 positioned between first and second windows 318a,318b. As will be described in more detail below, when tuning fork probe 300 is inserted into a tubular, for example, fluid within the tubular will flow through gap 320 as fluid sample 106. As electromagnetic radiation 110 conveys through gap 320, it is transmitted through fluid sample 106 to produce sample-interacted light 112.

Sample-interacted light 112 is then conveyed through second window 318b, positioned along second rod 308, and reflected off second reflective element 314b positioned at a second end 316b of second rod 308. Sample-interacted light 112 then travels along bore 310b and eventually encounters optical element 104 positioned at a first end 312b of second rod 308. Here, sample-interacted light 112 optically interacts with optical element 104 to produce optically-interacted light 122, which is related to the characteristic or analyte of interest. Optically-interacted light 122 is then conveyed to detectors 116,118,216 for generation of signal 124,128, which is then transmitted to a local or remote processor (not shown) for analysis and quantification of one or more desired characteristics of fluid sample 106.

Still referring to the exemplary embodiment of FIG. 3A, the various electromagnetic radiations conveyed through bores 310a,b may be conveyed in a variety of ways, including, for example, using wave guided or fiber optic methodologies. Thus, in one alternative embodiment, bores 310a,b each comprise one or more fiber optic cables positioned to convey the electromagnetic radiation.

The size of gap 320 is important for proper wave propagation. Therefore, in certain exemplary embodiments, the length of tuning fork probe 300 is roughly on the order of 1-2 inches and its total diameter is roughly 0.8" (20 mm), and electromagnetic radiation 110 and sample-interacted light 112 each have a total beam diameter of roughly 0.25". In such embodiments, the size of gap 320 is between 5-25 mm. As will be understood by those ordinarily skilled in the art having the benefit of this disclosure, if gap 320 is too small, there is a weakened light/sample interaction that impacts the detection capability. If gap 320 is too large, no light will propagate through gap 320. Therefore, the size of gap 320 is dependent upon the size of tuning fork probe 300, the electromagnetic radiation being conveyed, and the fluid's composition. Accordingly, those same ordinarily skilled persons will realize that the size of gap 320 may be larger or smaller than that described herein in alternative various designs.

In certain other exemplary embodiments, first and second windows 318a,318b may be removed when first and second rods 306,308 are comprised of sapphire, for example. Such embodiments are especially useful to avoid clogging gap 320 with matter (solids, for example) existing within fluid sample 106. Also, since first and second windows 318a,b must be a certain thickness to withstand downhole pressures, gap 320 may be too small and, thus, unnecessarily restrict the amount fluid sample 106 allowed to flow therethrough. Therefore, by utilizing sapphire rods, first and second windows 318a,b may be removed and replaced by windows formed by the sapphire material of the rods themselves at second ends 316a,b.

FIG. 3B illustrates a sectional view of a tubular 322 having a plurality of tuning fork probes 300 positioned radially around the body of tubular 322, according to certain exemplary embodiments of the present invention. Tubular 322 may be a variety of fluid-containing bodies, including, for example, downhole well tubulars, pipelines, or storage containers. In this embodiment, tubular 322 is 10' long and the total diameter of tuning fork probes 300 is 0.8". However, other dimensions may be utilized for larger or smaller sized tubulars. In one exemplary embodiment as shown, first and second rods 306,308 extend into tubular 322 in a direction such that axis A of first and second rods 306,308 are substantially parallel to axis B of tubular 322 and the direction of the flow of the fluid C. In an alternative exemplary embodiment, however, tuning fork probe 300 may be inserted into tubular 322 in a direction such than axis A is substantially perpendicular to axis B of tubular body 322.

Nevertheless, in either embodiment (parallel or perpendicular insertion), tuning fork probe 300 should not intrude upon the center space D extending along the length of tubular 322. Center space D is utilized to convey various tools down through tubular 322 during downhole operations; therefore, tuning fork probe 300 must not infringe on such conveyances as to avoid damage to itself or the tools. In an alternative embodiment, however, tuning fork probe 300 may comprise an extension mechanism which extends it out into center space D when desired, and then retracts it back out of center space D when necessary. Such an extension mechanism may be, for example, an external spring loaded, remotely triggered, mechanical jacking device.

Still referring to FIG. 3B, tuning fork probes 304 may be coupled to tubular 322 in a variety of ways. For example, tubular 322 may comprise a port having a threaded connection to receive a mating connection located on the exterior of tuning fork probes 300. Alternatively, tuning fork probe 300 may be welded to tubular 322. As shown in FIG. 3B, housings 304 are illustrated as partially inside and outside of tubular 322. Alternatively, housing 304 may be completely outside tubular 322. Also, in certain embodiments, housing 304 may be removably attached to tubular 322 so that electromagnetic radiation source 108, optical element 104, detectors 116,118,216 and system electronics may be repair or replaced. Also, in such embodiments, first and second rods 306,308 may be attached directly to tubular 322, so that they remain in place during servicing. In yet other embodiments, first and second rods 306,308 may also be removably attached to tubular 322. Ultimately, those ordinarily skilled in the art having the benefit of this disclosure realize there are a variety of features which may be combined as desired within the present invention.

During operation of the embodiment illustrated in FIG. 3B, fluid C flows through tubular 322 in the direction indicated by the arrow. As fluid C flows inside tubular 322, it flows out and around tuning fork probes 300 such that a portion of fluid C, or fluid sample 106, flows through gap 320 between first and second rods 306,308, as previously described. Once tuning fork probes 300 are activated, they determine one or more characteristics of fluid C utilizing the optical components described herein. Moreover, although not shown, tuning fork probes 300 may be in wired/wireless communication with one another and/or some remote processing station. Additionally, each tuning fork probe 300 may be operated in a distributed network type fashion as described in Patent Cooperation Treaty Application No. PCT/US2013/4146877, filed on Jun. 20, 2013, entitled "INTEGRATED COMPUTATIONAL ELEMENT-BASED OPTICAL SENSOR NETWORK AND RELATED METHODS, the disclosure of which is hereby incorporated by reference in its entirety.

Figure 4:
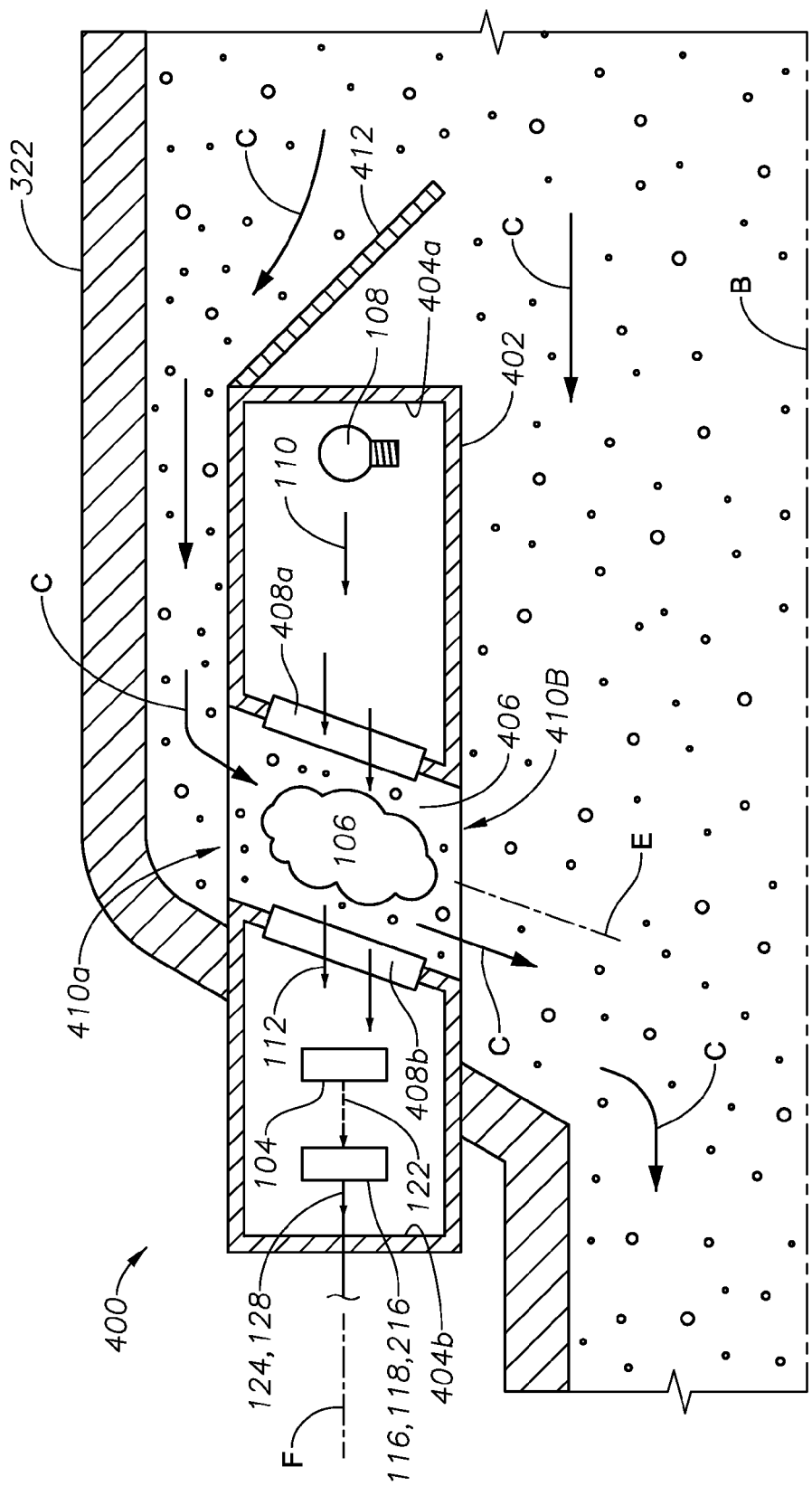
FIG. 4 illustrates a sectional block diagram of a spark plug probe implementation of an optical computing device, according to certain exemplary embodiments of the present invention.

FIG. 4 illustrates a sectional block diagram of a spark plug probe 400 implementation of optical computing device 100,200 according to certain exemplary embodiments of the present invention. Like the other embodiments described herein, spark plug probe 400 may be utilized in a variety of applications. Nevertheless, the following description will focus on the use of spark plug probe 400 with tubular 322. As previously stated, tubular 322 may be any variety of fluid-containing bodies, such as, for example, a downhole well tubular, pipeline or storage container. Spark plug probe 400 comprises a probe body 402 adapted to be extended into a body, such as, for example, tubular 322. Probe body 402 may be, for example, a hollow tubular shaped body sealed at both ends and made of temperature/pressure resistant material including, for example, stainless steels and their alloys, titanium and other high strength metals, and even carbon fiber composites and sapphire or diamond structures, as understood in the art. In this exemplary embodiment, probe body 402 has a diameter of roughly 0.8" (20 mm) and may be any desired length, although other dimensions may also be utilized.

First end 404 of probe body 402 extends inside tubular 14 whereby electromagnetic radiation source 108 is positioned. A flow channel 406 extends through probe 402 so that fluid sample 106 of fluid C may flow therethrough during sensing operations. Flow channel 406 includes inlet port 410a in which fluid sample 106 enters, and outlet port 410b in which fluid sample 106 exits and returns to fluid C. Thus, flow channel 406 is akin to a tunnel extending through probe body 402. The diameter of flow channel 406 may also be referred to as the gap which, in certain exemplary embodiments, is roughly 1" while the diameter of the electromagnetic radiation emanating across flow channel 406 is roughly 0.5", although other dimensions may be utilized. Thus, one advantage of this embodiment is that the width of the gap (flow channel 406) can be pre-set regardless of a given tubular diameter without adding additional complexity to the design of spark plug probe 400.

In certain embodiments, flow channel 406 extends through probe body 402 along axis E that traverses axis F of probe body 402 at an angle suitable to ease the flow of fluid sample 106. In one exemplary embodiment, the angle may be, for example, 45 degrees in order to minimize the dimensions of windows 408a,b, while also optimizing flow characteristics within flow channel 406. However, those ordinarily skilled in the at having the benefit of this disclosure will realize other angles may be utilized as dictated by the probe design and fluid characteristics. Nevertheless, first and second optical windows 408a,b are positioned along either side of flow channel 404 to convey electromagnetic radiation during operations. Adjacent a second end 404b of probe body 402 are optical element 104 and detectors 116,118,216. Other system electronics (processor, for example) necessary for operations and/or communication may also be housed within probe body 402. Moreover, a diverter 412 may be positioned at first end 404a to divert the flow of fluid C towards inlet port 410a.

As described in relation to other embodiments herein, a plurality of spark plug probes 400 may be positioned radially around the body of tubular 322, as was described in relation to FIG. 3B. Each may be coupled to tubular 322 in a variety of ways, including threaded connections along the exterior of probe body 402 and an insertion port along tubular 322, welding, etc. In one exemplary embodiment, spark plug probes 400 extend into tubular 322 such that an axis F of probe body 402 is substantially parallel to axis B of tubular 322, as shown in FIG. 4. In other embodiments, spark plug probes 400 may extend into tubular 322 such that axis F is substantially perpendicular to axis B. In either embodiment, as with other embodiments described herein, spark plug probe 400 does not extend out into center space D (shown in FIG. 3B). In yet other exemplary embodiments, extension mechanisms may be utilized to extend and retract spark plug probe 400 into and out of center space D as desired.

As shown in FIG. 4, probe body 402 is illustrated as partially inside and outside of tubular 322. A removable cap (not shown) may be positioned along second end 404b of probe body 402 to allow access to internal circuitry and other components for servicing. In certain embodiments, probe body 402 may be removably attached to tubular 322 or may be permanently attached. Additionally, when multiple spark plug probes are used, they may be operated in a network type fashion as previously described. Ultimately, those ordinarily skilled in the art having the benefit of this disclosure realize there are a variety of features which may be combined as desired within the present invention.

During operation of spark plug probe 400, fluid C is allowed to flow through tubular 322 whereby it encounters diverter 412 that diverts fluid C towards inlet port 410a. Inlet port 410 essentially extracts fluid sample 106 from fluid C whereby it flows through flow channel 406 and is then returned to fluid C via outlet port 410b. As it flows through flow channel 406, electromagnetic radiation source 108 emits electromagnetic radiation 110 toward first window 408a where it is conveyed onto to fluid sample 106. Here, it optically interacts with fluid sample 106 to produce sample-interacted light 112, which is then conveyed through second window 408b positioned along flow channel 406 opposite of first window 408a. Sample-interacted light 112 is then conveyed onto optical element 104 where it is optically interacted to produce optically-interacted light 122 that corresponds to one or more characteristics of fluid sample 106. Optically-interacted light 122 is then conveyed onto to detectors 116,118,216, whereby optically-interacted light 122 is measured to generate signal 124,128 utilized to determine the characteristic(s) of fluid sample 106. Signal 124,128 may then be transmitted, via wired/wireless methods, to a remote or local processor for further analysis.

FIG. 5A illustrates a sectional block diagram of a grooved tubular 500 implementation of optical computing device 100,200 according to certain exemplary embodiments of the present invention. Again, grooved tubular 500 may be utilized in a variety of applications. Nevertheless, the following description will focus on the use of grooved tubular 500 in an oil and gas related application such as, for example, a pipeline or downhole well tubular. Alternatively, grooved tubular 500 may be implemented as some other fluid-containing body utilized to store or otherwise transport fluid. Grooved tubular 500 comprises a tubular body 502 having a bore 504 extending therethrough. An optical groove 506 extends along the surface of bore 504 in which fluid sample 106 of fluid C is allowed to flow. Optical groove 506 may extend along the entire length of tubular body 502 or only of portion of it. Although optical groove 506 is positioned at the top of grooved tubular 500, it may be positioned at any desired location around tubular body 502 in alternate embodiments.

On both sides of optical groove 506 are two pockets 508a and 508b in which various system electronics and components may be housed. Electromagnetic radiation source 108 is positioned within pocket 508a along tubular body 502 adjacent to optical groove 506, to thereby emit electromagnetic radiation 110 across optical groove 506 during sensing operations. In this manner, optical groove 506 works as the gap previously described. In one exemplary embodiment, optical groove 506 has a width of roughly 0.8" (20 mm); although other dimensions may be utilized as described previously. First and second windows 510a and 510b, respectively, are positioned on either side of optical groove 506 to convey the electromagnetic radiation. Optical element 104 is positioned within pocket 508b to receive sample-interacted light 112 via second window 510b. Detector 116,118,216 is then positioned to receive optically interacted light 122 from optical element 104 and produce signal 124,128 as previously described, which may then be transmitted to a local or remote processor for further analysis.

In certain other exemplary embodiments of grooved tubular 500, a plurality of electromagnetic radiation sources 108 and associated optical elements, detectors, etc. may extend along optical groove 506, as illustrated in FIG. 5B. FIG. 5B illustrates a sectional view of the length of grooved tubular 500 having a plurality of pockets 508 (and their associated optical components) positioned down the extent of tubular body 502. In certain other embodiments, each pocket 508 (and its associated optical components) are optimized to detect one of a plurality of characteristics of fluid sample 106. In yet other embodiments, a plurality of optical grooves 506 may be positioned around tubular body 502 wherein each of them includes one or more electromagnetic radiation source 108 and associated optical elements, detectors, etc. Moreover, in others, optical groove 506 may spiral around the surface of bore 504 akin to a screw thread. Although not illustrated, grooved tubular 500, or any of the other embodiments described herein, may include a pressure balancing system to balance the pressure inside pockets 508a,b and the downhole environment.

During operation of grooved tubular 500, fluid C is allowed to flow through bore 504 whereby fluid sample 106 flows along one or more optical grooves 506. As the fluid flows therethrough, electromagnetic radiation source 108 emits electromagnetic radiation 110 toward first window 510a, whereby it traverses axis G (FIG. 5B) of optical groove 506 to encounter fluid sample 106 to produce sample-interacted light 112. Sample-interacted light 112 then emanates through second window 510b and on to optical element 104, where it optically interacts to produce optically-interacted light 122 which corresponds to one or more characteristics of fluid sample 106. Optically-interacted light 122 then encounters detector 116,118,216 which generates signal 124,128 utilized to determine the characteristic of fluid sample 106. Signal 124,128 may then be transmitted to a remote or local processor for further processing.

In certain other exemplary embodiments of grooved tubular 500, optical groove 506 may comprise a variety of shapes. Exemplary shapes include, for example, a "V" shape (FIG. 5C) or a rounded shape (FIG. 5D). FIGS. 5C and 5D are sectional simplified views of grooved tubular 500 intended to illustrate alternative profile shapes for optical groove 506. FIG. 5E is yet another sectional simplified view of optical groove 506 intended to illustrate how certain embodiments of optical groove 506 tapers into bore 504. As shown, the lower ends 506a,b gradually transitions, or tapers, between the profile of optical groove 506 to the cylindrical profile of bore 504. Such a gradual transition minimizes the perturbations of fluid sample 106 through optical groove 506. Alternatively, abrupt transitions, or sharp edges such as illustrated in FIGS. 5A-5D, are useful to induce perturbations in the flow of fluid sample 106.

Figure 6B:
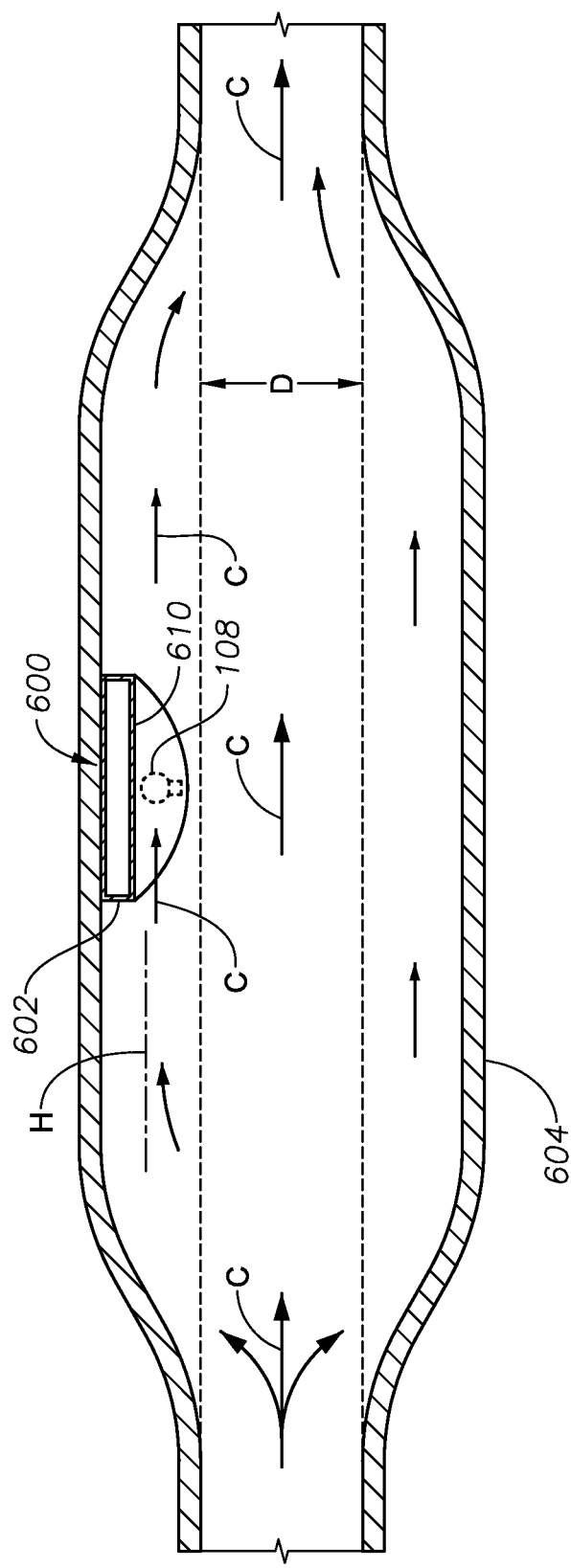

FIGS. 6A and 6B illustrate a sectional block diagram of a module 600 implementation and a sectional view along the length of module 600, respectively, of optical computing device 100,200 according to certain exemplary embodiments of the present invention. As previously described, module 600 may be utilized within a variety of application environments, such as, for example, within a pipeline, downhole well tubular or other fluid-containing body. Nevertheless, the following description will focus on the use of module 600 within a downhole well tubular.

As shown in FIG. 6B, module 600 is a modular-type optical computing device comprising a device housing 602 which permanently or removably attaches to the surface of a bore 606 extending through a fluid-containing body, such as a tubular 604. Device housing 602 may be a high temperature/pressure housing which is self-contained such that all circuitry, optical components, power supply, etc., are housed within device housing 602. A variety of materials may be utilized for device housing 602, including, for example, stainless steels and their alloys, titanium and other high strength metals, and even carbon fiber composites and sapphire or diamond structures, as understood in the art. Although module 600 is comprises a dome-type shape, it may also take a variety of other modular shapes. The upper portion 608 of device housing 602 is shaped to mate with the curvature of tubular 604. Nevertheless, module 600 may be attached to the surface of bore 604 using a variety of methods, such as, for example, magnetism or welding. Moreover, module 600 is positioned such that it does not infringe into center space D where various downhole tools are conveyed.

Module 600 includes an optical groove 610 positioned along the exterior of device housing 602 in which fluid sample 106 may flow. Optical groove 610 again acts as the gap previously described herein which, in this exemplary embodiment, has width of roughly 0.8". However, other dimensions may be utilized as understood by those ordinarily skilled persons described herein. On either side of optical groove 610 are first and second optical windows 612a and 612b, respectively, through which electromagnetic radiation may be conveyed. Electromagnetic radiation source 108 is positioned inside device housing adjacent to optical groove 610, while optical element 104 and detector 116,118,216 are positioned on the opposite side of optical groove 610 to receive sample-interacted light 112. In this embodiment, electromagnetic radiation source 108 emits electromagnetic radiation 110 across optical groove 610 such that it traverses axis H (FIG. 6B) of optical groove 610.

In certain alternative exemplary embodiments of module 600, the profile of optical groove 610 may be, for example, a "V" shape or rounded shape as shown in FIGS. 5C and 5D. Also, optical groove 610 may also taper into the cylindrical profile of bore 606 as previously described herein. In other embodiments, multiple electromagnetic radiation sources 108 and associated optical elements and detectors may be positioned along optical groove 610 to determine one or more additional characteristics of fluid sample 106. In other embodiments a plurality of modules 600 may be positioned around more 606 to detect fluid samples at various positions along bore 606. Moreover, although not shown, module 600 may comprise telemetry circuitry to perform various communication operations. Also, as previously described herein, if a plurality of modules 600 are positioned throughout an environment (well, for example), they may be in communication with one another or some central processing station, for example, in a distributed network fashion to perform various sensing or power reserve operations (on/off cycling of modules 660, for example). Furthermore, optical groove 610 may be replaced with an internal reflectance element utilized to produce sample-interacted light, as will be understood by those ordinarily skilled in the art having the benefit of this disclosure.

With reference to FIGS. 6A and 6B, during operation of module 600, fluid C is allowed to flow through tubular 604 whereby fluid sample 106 passes along optical groove 610. As the fluid flows therethrough, electromagnetic radiation source 108 emits electromagnetic radiation 110 toward first window 612a, whereby it traverses axis H (FIG. 6B) of optical groove 610 to encounter fluid sample 106 to produce sample-interacted light 112. Sample-interacted light 112 then emanates through second window 612b and on to optical element 104, where it optically interacts to produce optically-interacted light 122 which corresponds to one or more characteristics of fluid sample 106. Optically-interacted light 122 then encounters detector 116,118,216 which generates signal 124,128 utilized to determine the characteristic of fluid sample 106. Although signals 124,128 are shown as being transmitted remotely in FIG. 6B, they may also be processed locally in those embodiments in which all processing circuitry is housed in module 600.

As described herein, each implementation of optical computing devices 100,200 may be utilized to determine a variety of characteristics, such as, for example, the presence and quantity of specific inorganic gases such as, for example, $CO_2$ and $H_2S$, organic gases such as methane (C1), ethane (C2) and propane (C3) and saline water, in addition to dissolved ions (Ba, Cl, Na, Fe, or Sr, for example) or various other characteristics (p.H., density and specific gravity, viscosity, total dissolved solids, sand content, etc.). Furthermore, the presence of formation characteristic data (porosity, formation chemical composition, etc.) may also be determined. In certain embodiments, a single optical computing device may detect a single characteristic, while in others a single optical computing device may determine multiple characteristics, as will be understood by those ordinarily skilled in the art having the benefit of this disclosure.

Accordingly, the present invention provides various implementations of optical computing devices to determine one or more characteristics of a sample in real-time by deriving the data directly from the output of an optical element. The present invention provides a number of advantages, including, for example, low power requirements, robustness, minimized impact of fluid flow characteristics, the ability to place and retrieve the optical system for maintenance or evolutionary upgrades, and allowing the passage of other downhole equipment pass the optical sensor.

An exemplary embodiment of the present invention provides an optical computing device to determine a characteristic of a fluid sample, the device comprising a probe body adapted for use along a tubular body, the probe body comprising a first rod extending into the tubular body; and a second rod extending into the tubular body adjacent the first rod, thereby forming a gap between the first and second rods wherein the sample fluid may flow; electromagnetic radiation that optically interacts with the fluid sample flowing through the gap to thereby produce sample-interacted light; an optical element that optically interacts with the sample-interacted light to produce optically-interacted light which corresponds to the characteristic of the fluid sample; and a detector positioned to measure the optically-interacted light and thereby generate a signal utilized to determine the characteristic of the fluid sample. In another, the first and second rods each comprise a bore extending therethrough that is defined by a first end and a second end opposite the first end, the bores of the first and second rods being adapted to convey the electromagnetic radiation to the fluid sample, the sample-interacted light to the optical element, and the optically-interacted light to the detector.

In another, the bores of the first and second rods each comprise a fiber optic cable to convey the electromagnetic radiation, sample-interacted light and the optically interacted light. In yet another, the first and second rods each comprise a bore extending therethrough that is defined by a first end and second end opposite the first end, the optical computing device further comprising an electromagnetic radiation source positioned adjacent the first end of the first rod, the electromagnetic radiation source adapted to generate the electromagnetic radiation; a first reflective element positioned adjacent a second end of the first rod to thereby reflect the electromagnetic radiation across the gap to produce the sample-interacted light; and a second reflective element positioned adjacent the second end of the second rod to thereby receive the sample-interacted light and convey the sample interacted light along the bore of the second rod towards the optical element, wherein the optical element and detector are positioned adjacent the first end of the second rod. Another further comprises a first window positioned along the first rod adjacent the first reflective element; and a second window positioned along the second rod adjacent the second reflective element, wherein the gap is formed between the first and second windows.

In another, the first and second rods extend into the tubular body in a direction such that an axis of the rods is substantially parallel to an axis of the tubular body and a direction of flow of the fluid sample. In yet another, the first and second rods extend into the tubular body in a direction such that an axis of the rods is substantially perpendicular to an axis of the tubular body and a direction of flow of the fluid sample. In another, the computing device further comprises an electromagnetic radiation source adapted to generate the electromagnetic radiation, wherein the electromagnetic radiation source, optical element and detector are positioned outside the tubular. In another, the electromagnetic radiation source, optical element and detector are removably attached to the tubular. In yet another, the first and second rods are removably attached to the tubular. In yet another, the first and second rods are comprised of at least one of aluminum, sapphire, glass, diamond, ZnSe, ZnS, Ge or Si.

In yet another, the optical computing device further comprises a signal processor communicably coupled to the detector to computationally determine the characteristic of the fluid sample. In another, the optical element is an Integrated Computational Element. In yet another, the characteristic of the fluid sample is at least one of a C1-C6 hydrocarbon, salinity, sand content, pH, total dissolved solids, H2S, CO2, asphaltenes, waxes, saturates, resins or water. In yet another, the tubular is a pipeline or downhole well tubular.

An exemplary methodology of the present invention provides a method utilizing an optical computing device to determine a characteristic of a fluid sample, the method comprising positioning the optical computing device along a tubular body, the optical computing device having a probe body comprising a first rod extending into the tubular body; and a second rod extending into the tubular body adjacent the first rod, thereby forming a gap between the first and second rods wherein the fluid sample may flow; optically interacting electromagnetic radiation with the fluid sample flowing through the gap to produce sample-interacted light; optically interacting an optical element with the sample-interacted light to generate optically-interacted light which corresponds to a characteristic of the fluid sample; generating a signal that corresponds to the optically-interacted light through utilization of a detector; and determining a characteristic of the fluid sample using the signal. In another, optically interacting electromagnetic radiation with the fluid sample further comprises conveying the electromagnetic radiation through a bore extending along the first rod and on to the fluid sample to produce the sample-interacted light.

In yet another, optically interacting the optical element with the sample-interacted light further comprises conveying the sample-interacted light through a bore extending along the second rod and on to the optical element to generate the optically-interacted light. In another, positioning the optical computing device further comprises positioning the optical computing device along a pipeline or downhole well tubular. In yet another, positioning the optical computing device further comprises positioning a plurality of optical computing devices at various radial positions around the tubular body.

Another exemplary embodiment of the present invention provides an optical computing device to determine a characteristic of a fluid sample, the device comprising a probe body adapted for use along a tubular body, the probe body comprising a first end that extends into the tubular body; and a flow channel through which the fluid sample may flow, the flow channel extending through the probe body along an axis that traverses an axis of the probe body; electromagnetic radiation that optically interacts with the fluid sample flowing through the flow channel to thereby produce sample-interacted light; an optical element that optically interacts with the sample-interacted light to produce optically-interacted light which corresponds to the characteristic of the fluid sample; and a detector positioned to measure the optically-interacted light and thereby generate a signal utilized to determine the characteristic of the fluid sample. In another, the optical computing device further comprises an electromagnetic radiation source positioned adjacent the first end of the probe body, the electromagnetic radiation source adapted to generate the electromagnetic radiation, wherein the optical element and detector are positioned inside the probe body adjacent a second end of the probe body opposite the first end.

In yet another, the computing device further comprises a first window positioned along the flow channel to convey the electromagnetic radiation emanating from the electromagnetic radiation source; and a second window positioned along the flow channel at a position opposite the first window to thereby convey the sample-interacted light to the optical computing device. In another, the flow channel comprises an inlet port to extract the fluid sample from fluid flowing through the tubular; an outlet port to return the fluid sample back to the fluid flowing through the tubular; and a diverter positioned at the first end of the probe body to divert the fluid towards the inlet port. In yet another, the axis of the flow channel traverses the axis of the probe body at an angle. In another, the probe body extends into the tubular such that an axis of the probe body is substantially parallel to an axis of the tubular body and a direction of flow of fluid through the tubular. In yet another, the second end of the probe body extends outside the tubular body. In another, the optical computing device is removably attached to the tubular body.

In yet another, the computing device further comprises a signal processor communicably coupled to the detector to computationally determine the characteristic of the fluid sample. In another, the optical element is an Integrated Computational Element. In another, the characteristic of the fluid sample is at least one of a C1-C6 hydrocarbon, salinity, sand content, pH, total dissolved solids, H2S, CO2, asphaltenes, waxes, saturates, resins or water. In yet another, the tubular is a pipeline or downhole well tubular.

Another exemplary methodology of the present invention provides a method utilizing an optical computing device to determine a characteristic of a fluid sample, the method comprising positioning the optical computing device along a tubular body, the optical computing device having a probe body comprising a first end that extends into the tubular body; and a flow channel through which the fluid sample may flow, the flow channel extending through the probe body along an axis that traverses an axis of the probe body; optically interacting electromagnetic radiation with the fluid sample flowing through the flow channel to produce sample-interacted light; optically interacting an optical element with the sample-interacted light to generate optically-interacted light which corresponds to a characteristic of the fluid sample; generating a signal that corresponds to the optically-interacted light through utilization of a detector; and determining a characteristic of the fluid sample using the signal.

In another, optically interacting electromagnetic radiation with the fluid sample further comprises conveying the electromagnetic radiation from an electromagnetic radiation source positioned adjacent the first end of the probe body and on to the flow channel. In yet another, optically interacting the optical element with the sample-interacted light further comprises conveying the sample-interacted light to the optical element positioned adjacent a second end of the probe body opposite the first end. In another, optically interacting the electromagnetic radiation with the fluid sample flowing through the flow channel further comprises diverting fluid flowing through the tubular towards an inlet port of the flow channel utilizing a diverter positioned at the first end of the probe body; extracting the fluid sample from the diverted fluid using the inlet port, whereby the fluid sample flows through the flow channel; and returning the fluid sample back to the fluid flowing through the tubular.

In another, positioning the optical computing device along the tubular body further comprises extending the probe body into the tubular such that an axis of the probe body is substantially parallel to an axis of the tubular body and a direction of fluid flow through the tubular. In yet another, positioning the optical computing device further comprises positioning the optical computing device along a pipeline or downhole well tubular. In another, positioning the optical computing device further comprises positioning a plurality of optical computing devices at various radial positions around the tubular body. In yet another, determining the characteristic of the fluid sample further comprises determining a presence of at least one of a C1-C6 hydrocarbon, salinity, sand content, pH, total dissolved solids, H2S, CO2, asphaltenes, waxes, saturates, resins or water.

Another exemplary embodiment of the present invention provides an optical computing device to determine a characteristic of a fluid sample, the device comprising a tubular body having a bore extending therethrough; an optical groove extending along a surface of the bore in which a fluid sample of the fluid may flow; electromagnetic radiation that optically interacts with the fluid sample flowing through the optical groove to thereby produce sample-interacted light; an optical element that optically interacts with the sample-interacted light to produce optically-interacted light which corresponds to the characteristic of the fluid sample; and a detector positioned to measure the optically-interacted light and thereby generate a signal utilized to determine the characteristic of the fluid sample. In another, the computing device further comprises an electromagnetic radiation source positioned along the tubular body adjacent to the optical groove, the electromagnetic radiation source being adapted to generate the electromagnetic radiation, wherein the optical element is positioned along the tubular body adjacent to the optical groove such that the optical element receives the sample-interacted light emanating from the fluid sample.

In another, the electromagnetic radiation source emits the electromagnetic radiation in a direction such that the electromagnetic radiation traverses an axis of the optical groove. In yet another, the optical groove has a "V" shape, a squared shape or a rounded shape. In yet another, the optical groove tapers into the bore. In another, the optical groove spirals around the surface of the bore. In yet another, the computing device further comprises multiple electromagnetic radiation sources and associated optical elements extending along the optical groove. Another further comprises multiple optical grooves extending along the surface of the bore, each optical groove having at least one electromagnetic radiation source and associated optical element. Yet another further comprises a signal processor communicably coupled to the detector to computationally determine the characteristic of the fluid sample. In yet another embodiment, the optical element is an Integrated Computational Element. In another, the characteristic of the fluid sample is at least one of a C1-C6 hydrocarbon, salinity, sand content, pH, total dissolved solids, H2S, CO2, asphaltenes, waxes, saturates, resins or water. In yet another, the tubular body is a pipeline or downhole well tubular.

Another exemplary methodology of the present invention provides a method utilizing an optical computing device to determine a characteristic of a fluid sample, the method comprising deploying the optical computing device into an environment, the optical computing device comprising a tubular body having a bore extending therethrough; and an optical groove extending along a surface of the bore in which a fluid sample of the fluid may flow; optically interacting electromagnetic radiation with the fluid sample flowing through the optical groove to produce sample-interacted light; optically interacting an optical element with the sample-interacted light to generate optically-interacted light which corresponds to a characteristic of the fluid sample; generating a signal that corresponds to the optically-interacted light through utilization of a detector; and determining a characteristic of the fluid sample using the signal. In another, optically interacting the electromagnetic radiation with the fluid sample further comprises conveying the electromagnetic radiation from an electromagnetic radiation source positioned along the tubular body adjacent the optical groove, the electromagnetic radiation being conveyed in a direction that traverses an axis of the optical groove.

In yet another, optically interacting the optical element with the sample-interacted light further comprises conveying the sample-interacted light to the optical element positioned along the tubular body adjacent to the optical groove opposite the electromagnetic radiation source. In another, deploying the optical computing device into the environment further comprises deploying a plurality of optical computing devices into the environment, the plurality of optical computing devices each comprising electromagnetic radiation sources and associated optical elements extending along the optical groove. In another, deploying the optical computing device into the environment further comprises deploying the optical computing device as a pipeline or a downhole well tubular. In yet another, determining the characteristic of the fluid sample further comprises determining a presence of at least one of a C1-C6 hydrocarbon, salinity, sand content, pH, total dissolved solids, H2S, CO2, asphaltenes, waxes, saturates, resins or water.

Another exemplary embodiment of the present invention provides an optical computing device to determine a characteristic of a fluid sample, the device comprising a device housing that attaches to a surface of a fluid-containing body; an optical groove positioned on an exterior of the device housing along which a fluid sample may flow; electromagnetic radiation that optically interacts with the fluid sample flowing along the optical groove to thereby produce sample-interacted light; an optical element positioned inside the device housing to optically interact with the sample-interacted light to produce optically-interacted light which corresponds to the characteristic of the fluid sample; and a detector positioned inside the device housing to measure the optically-interacted light and thereby generate a signal utilized to determine the characteristic of the fluid sample. In another, the device housing is dome-shaped. In yet another, the optical groove is an internal reflectance element.

In another, the computing device further comprises an electromagnetic radiation source positioned inside the device housing adjacent to the optical groove, the electromagnetic radiation source being adapted to generate the electromagnetic radiation, wherein the optical element is positioned adjacent to the optical groove such that the optical element receives the sample-interacted light emanating from the fluid sample. In another, the electromagnetic radiation source emits the electromagnetic radiation in a direction such that the electromagnetic radiation traverses an axis of the optical groove. In yet another, the optical groove has a "V" shape, a squared shape or a rounded shape. In another, the optical groove tapers into the device housing. In yet another, the computing device further comprises multiple electromagnetic radiation sources and associated optical elements extending along the optical groove.

In another, the computing device a signal processor communicably coupled to the detector to computationally determine the characteristic of the fluid sample. In yet another, the optical element is an Integrated Computational Element. In another, the characteristic of the fluid sample is at least one of a C1-C6 hydrocarbon, salinity, sand content, pH, total dissolved solids, H2S, CO2, asphaltenes, waxes, saturates, resins or water. In yet another, the fluid-containing body is a pipeline or downhole well tubular. In yet another, the optical computing device is removably attached to the surface of the fluid-containing body.

Another exemplary methodology of the present invention provides a method utilizing an optical computing device to determine a characteristic of a fluid sample, the method comprising attaching the optical computing device to a surface of a fluid-containing body, the optical computing device comprising a device housing that attaches to the surface of the fluid-containing body; and an optical groove positioned on an exterior of the device housing along which a fluid sample may flow; optically interacting electromagnetic radiation with the fluid sample flowing along the optical groove to produce sample-interacted light; optically interacting an optical element with the sample-interacted light to generate optically-interacted light which corresponds to a characteristic of the fluid sample; generating a signal that corresponds to the optically-interacted light through utilization of a detector; and determining a characteristic of the fluid sample using the signal.

In another, optically interacting electromagnetic radiation with the fluid sample further comprises conveying the electromagnetic radiation from an electromagnetic radiation source positioned inside the device housing adjacent to the optical groove, the electromagnetic radiation being conveyed in a direction such that the electromagnetic radiation traverses an axis of the optical groove. In yet another, optically interacting the optical element with the sample-interacted light further comprises conveying the sample-interacted light to the optical element positioned along the device housing adjacent to the optical groove opposite the electromagnetic radiation source. In another, attaching the optical computing device to the surface of the fluid-containing body further comprises attaching a plurality of optical computing devices to the surface of the fluid-containing body, the plurality of optical computing devices each comprising electromagnetic radiation sources and associated optical elements extending along the optical groove. In yet another, attaching the optical computing device to the surface of the fluid-containing body further comprises attaching at least one optical computing device to a surface of a pipeline or a downhole well tubular. In yet another, determining the characteristic of the fluid sample further comprises determining a presence of at least one of a C1-C6 hydrocarbon, salinity, sand content, pH, total dissolved solids, H2S, CO2, asphaltenes, waxes, saturates, resins or water.

Although various embodiments and methodologies have been shown and described, the invention is not limited to such embodiments and methodologies, and will be understood to include all modifications and variations as would be apparent to one ordinarily skilled in the art. Therefore, it should be understood that the invention is not intended to be limited to the particular forms disclosed. Rather, the intention is to cover all modifications, equivalents and alternatives falling within the spirit and scope of the invention as defined by the appended claims.

What is claimed is:

1. An optical computing device to determine a characteristic of a fluid sample, the device comprising:
    a probe body adapted for use along a tubular body, the probe body comprising:
        a first rod extending into the tubular body; and
        a second rod extending into the tubular body adjacent the first rod, thereby forming a gap between the first and second rods wherein the sample fluid may flow;
    electromagnetic radiation that optically interacts with the fluid sample flowing through the gap to thereby produce sample-interacted light;
    an optical element that optically interacts with the sample-interacted light to produce optically-interacted light which corresponds to the characteristic of the fluid sample; and
    a detector positioned to measure the optically-interacted light and thereby generate a signal utilized to determine the characteristic of the fluid sample.

2. An optical computing device as defined in claim 1, wherein the first and second rods each comprise a bore extending therethrough that is defined by a first end and a second end opposite the first end, the bores of the first and second rods being adapted to convey the electromagnetic radiation to the fluid sample, the sample-interacted light to the optical element, and the optically-interacted light to the detector.

3. An optical computing device as defined in claim 2, wherein the bores of the first and second rods each comprise a fiber optic cable to convey the electromagnetic radiation, sample-interacted light and the optically interacted light.

4. An optical computing device as defined in claim 1, wherein the first and second rods each comprise a bore extending therethrough that is defined by a first end and second end opposite the first end, the optical computing device further comprising:
    an electromagnetic radiation source positioned adjacent the first end of the first rod, the electromagnetic radiation source adapted to generate the electromagnetic radiation;
    a first reflective element positioned adjacent a second end of the first rod to thereby reflect the electromagnetic radiation across the gap to produce the sample-interacted light; and
    a second reflective element positioned adjacent the second end of the second rod to thereby receive the sample-interacted light and convey the sample interacted light along the bore of the second rod towards the optical element, wherein the optical element and detector are positioned adjacent the first end of the second rod.

5. An optical computing device as defined in claim 4, further comprising:
a first window positioned along the first rod adjacent the first reflective element; and
a second window positioned along the second rod adjacent the second reflective element, wherein the gap is formed between the first and second windows.

6. An optical computing device as defined in claim 1, wherein the first and second rods extend into the tubular body in a direction such that an axis of the rods is substantially parallel to an axis of the tubular body and a direction of flow of the fluid sample.

7. An optical computing device as defined in claim 1, wherein the first and second rods extend into the tubular body in a direction such that an axis of the rods is substantially perpendicular to an axis of the tubular body and a direction of flow of the fluid sample.

8. An optical computing device as defined in claim 1, further comprising an electromagnetic radiation source adapted to generate the electromagnetic radiation, wherein the electromagnetic radiation source, optical element and detector are positioned outside the tubular.

9. An optical computing device as defined in claim 8, wherein the electromagnetic radiation source, optical element and detector are removably attached to the tubular.

10. An optical computing device as defined in claim 1, wherein the first and second rods are removably attached to the tubular.

11. An optical computing device as defined in claim 1, wherein the first and second rods are comprised of at least one of aluminum, sapphire, glass, diamond, ZnSe, ZnS, Ge or Si.

12. An optical computing device as defined in claim 1, further comprising a signal processor communicably coupled to the detector to computationally determine the characteristic of the fluid sample.

13. An optical computing device as defined in claim 1, wherein the optical element is an Integrated Computational Element.

14. An optical computing device as defined in claim 1, wherein the characteristic of the fluid sample is at least one of a C1-C6 hydrocarbon, salinity, sand content, pH, total dissolved solids, H2S, CO2, asphaltenes, waxes, saturates, resins or water.

15. An optical computing device as defined in claim 1, wherein the tubular is a pipeline or downhole well tubular.

16. A method utilizing an optical computing device to determine a characteristic of a fluid sample, the method comprising:
positioning the optical computing device along a tubular body, the optical computing device having a probe body comprising:
a first rod extending into the tubular body; and
a second rod extending into the tubular body adjacent the first rod, thereby forming a gap between the first and second rods wherein the fluid sample may flow;
optically interacting electromagnetic radiation with the fluid sample flowing through the gap to produce sample-interacted light;
optically interacting an optical element with the sample-interacted light to generate optically-interacted light which corresponds to a characteristic of the fluid sample;
generating a signal that corresponds to the optically-interacted light through utilization of a detector; and
determining a characteristic of the fluid sample using the signal.

17. A method as defined in claim 16, wherein optically interacting electromagnetic radiation with the fluid sample further comprises conveying the electromagnetic radiation through a bore extending along the first rod and on to the fluid sample to produce the sample-interacted light.

18. A method as defined in claim 17, wherein optically interacting the optical element with the sample-interacted light further comprises conveying the sample-interacted light through a bore extending along the second rod and on to the optical element to generate the optically-interacted light.

19. A method as defined in claim 16, wherein positioning the optical computing device further comprises positioning the optical computing device along a pipeline or downhole well tubular.

20. A method as defined in claim 16, wherein positioning the optical computing device further comprises positioning a plurality of optical computing devices at various radial positions around the tubular body.

21. An optical computing device to determine a characteristic of a fluid sample, the device comprising:
a probe body adapted for use along a tubular body, the probe body comprising:
a first end that extends into the tubular body; and
a flow channel through which the fluid sample may flow, the flow channel extending through the probe body along an axis that traverses an axis of the probe body;
electromagnetic radiation that optically interacts with the fluid sample flowing through the flow channel to thereby produce sample-interacted light;
an optical element that optically interacts with the sample-interacted light to produce optically-interacted light which corresponds to the characteristic of the fluid sample; and
a detector positioned to measure the optically-interacted light and thereby generate a signal utilized to determine the characteristic of the fluid sample.

22. An optical computing device as defined in claim 21 further comprising an electromagnetic radiation source positioned adjacent the first end of the probe body, the electromagnetic radiation source adapted to generate the electromagnetic radiation, wherein the optical element and detector are positioned inside the probe body adjacent a second end of the probe body opposite the first end.

23. An optical computing device as defined in claim 22, further comprising:
a first window positioned along the flow channel to convey the electromagnetic radiation emanating from the electromagnetic radiation source; and
a second window positioned along the flow channel at a position opposite the first window to thereby convey the sample-interacted light to the optical computing device.

24. An optical computing device as defined in claim 21, wherein the flow channel comprises:
an inlet port to extract the fluid sample from fluid flowing through the tubular;
an outlet port to return the fluid sample back to the fluid flowing through the tubular; and
a diverter positioned at the first end of the probe body to divert the fluid towards the inlet port.

25. An optical computing device as defined in claim 24, wherein the axis of the flow channel traverses the axis of the probe body at an angle.

26. An optical computing device as defined in claim 21, wherein the probe body extends into the tubular such that an axis of the probe body is substantially parallel to an axis of the tubular body and a direction of flow of fluid through the tubular.

27. An optical computing device as defined in claim 22, wherein the second end of the probe body extends outside the tubular body.

28. An optical computing device as defined in claim 21, wherein the optical computing device is removably attached to the tubular body.

29. An optical computing device as defined in claim 21, further comprising a signal processor communicably coupled to the detector to computationally determine the characteristic of the fluid sample.

30. An optical computing device as defined in claim 21, wherein the optical element is an Integrated Computational Element.

31. An optical computing device as defined in claim 21, wherein the characteristic of the fluid sample is at least one of a C1-C6 hydrocarbon, salinity, sand content, pH, total dissolved solids, H2S, CO2, asphaltenes, waxes, saturates, resins or water.

32. An optical computing device as defined in claim 21, wherein the tubular is a pipeline or downhole well tubular.

33. A method utilizing an optical computing device to determine a characteristic of a fluid sample, the method comprising:
    positioning the optical computing device along a tubular body, the optical computing device having a probe body comprising:
        a first end that extends into the tubular body; and
        a flow channel through which the fluid sample may flow, the flow channel extending through the probe body along an axis that traverses an axis of the probe body;
    optically interacting electromagnetic radiation with the fluid sample flowing through the flow channel to produce sample-interacted light;
    optically interacting an optical element with the sample-interacted light to generate optically-interacted light which corresponds to a characteristic of the fluid sample;
    generating a signal that corresponds to the optically-interacted light through utilization of a detector; and
    determining a characteristic of the fluid sample using the signal.

34. A method as defined in claim 33, wherein optically interacting electromagnetic radiation with the fluid sample further comprises conveying the electromagnetic radiation from an electromagnetic radiation source positioned adjacent the first end of the probe body and on to the flow channel.

35. A method as defined in claim 34, wherein optically interacting the optical element with the sample-interacted light further comprises conveying the sample-interacted light to the optical element positioned adjacent a second end of the probe body opposite the first end.

36. A method as defined in claim 33, wherein optically interacting the electromagnetic radiation with the fluid sample flowing through the flow channel further comprises:
    diverting fluid flowing through the tubular towards an inlet port of the flow channel utilizing a diverter positioned at the first end of the probe body;
    extracting the fluid sample from the diverted fluid using the inlet port, whereby the fluid sample flows through the flow channel; and
    returning the fluid sample back to the fluid flowing through the tubular.

37. A method as defined in claim 33, wherein positioning the optical computing device along the tubular body further comprises extending the probe body into the tubular such that an axis of the probe body is substantially parallel to an axis of the tubular body and a direction of fluid flow through the tubular.

38. A method as defined in claim 33, wherein positioning the optical computing device further comprises positioning the optical computing device along a pipeline or downhole well tubular.

39. A method as defined in claim 33, wherein positioning the optical computing device further comprises positioning a plurality of optical computing devices at various radial positions around the tubular body.

40. A method as defined in claim 33, wherein determining the characteristic of the fluid sample further comprises determining a presence of at least one of a C1-C6 hydrocarbon, salinity, sand content, pH, total dissolved solids, H2S, CO2, asphaltenes, waxes, saturates, resins or water.

41. An optical computing device to determine a characteristic of a fluid sample, the device comprising:
    a tubular body having a bore extending therethrough;
    an optical groove extending along a surface of the bore in which a fluid sample of the fluid may flow;
    electromagnetic radiation that optically interacts with the fluid sample flowing through the optical groove to thereby produce sample-interacted light;
    an optical element that optically interacts with the sample-interacted light to produce optically-interacted light which corresponds to the characteristic of the fluid sample; and
    a detector positioned to measure the optically-interacted light and thereby generate a signal utilized to determine the characteristic of the fluid sample.

42. An optical computing device as defined in claim 41, further comprising an electromagnetic radiation source positioned along the tubular body adjacent to the optical groove, the electromagnetic radiation source being adapted to generate the electromagnetic radiation, wherein the optical element is positioned along the tubular body adjacent to the optical groove such that the optical element receives the sample-interacted light emanating from the fluid sample.

43. An optical computing device as defined in claim 42, wherein the electromagnetic radiation source emits the electromagnetic radiation in a direction such that the electromagnetic radiation traverses an axis of the optical groove.

44. An optical computing device as defined in claim 41, wherein the optical groove has a "V" shape, a squared shape or a rounded shape.

45. An optical computing device as defined in claim 41, wherein the optical groove tapers into the bore.

46. An optical computing device as defined in claim 41, wherein the optical groove spirals around the surface of the bore.

47. An optical computing device as defined in claim 41, further comprising multiple electromagnetic radiation sources and associated optical elements extending along the optical groove.

48. An optical computing device as defined in claim 41, further comprising multiple optical grooves extending along the surface of the bore, each optical groove having at least one electromagnetic radiation source and associated optical element.

49. An optical computing device as defined in claim 41, further comprising a signal processor communicably coupled to the detector to computationally determine the characteristic of the fluid sample.

50. An optical computing device as defined in claim 41, wherein the optical element is an Integrated Computational Element.

51. An optical computing device as defined in claim 41, wherein the characteristic of the fluid sample is at least one of a C1-C6 hydrocarbon, salinity, sand content, pH, total dissolved solids, H2S, CO2, asphaltenes, waxes, saturates, resins or water.

52. An optical computing device as defined in claim 41, wherein the tubular body is a pipeline or downhole well tubular.

53. A method utilizing an optical computing device to determine a characteristic of a fluid sample, the method comprising:
deploying the optical computing device into an environment, the optical computing device comprising:
a tubular body having a bore extending therethrough; and
an optical groove extending along a surface of the bore in which a fluid sample of the fluid may flow;
optically interacting electromagnetic radiation with the fluid sample flowing through the optical groove to produce sample-interacted light;
optically interacting an optical element with the sample-interacted light to generate optically-interacted light which corresponds to a characteristic of the fluid sample;
generating a signal that corresponds to the optically-interacted light through utilization of a detector; and
determining a characteristic of the fluid sample using the signal.

54. A method as defined in claim 53, wherein optically interacting the electromagnetic radiation with the fluid sample further comprises conveying the electromagnetic radiation from an electromagnetic radiation source positioned along the tubular body adjacent the optical groove, the electromagnetic radiation being conveyed in a direction that traverses an axis of the optical groove.

55. A method as defined in claim 54, wherein optically interacting the optical element with the sample-interacted light further comprises conveying the sample-interacted light to the optical element positioned along the tubular body adjacent to the optical groove opposite the electromagnetic radiation source.

56. A method as defined in claim 54, wherein deploying the optical computing device into the environment further comprises deploying a plurality of optical computing devices into the environment, the plurality of optical computing devices each comprising electromagnetic radiation sources and associated optical elements extending along the optical groove.

57. A method as defined in claim 53, wherein deploying the optical computing device into the environment further comprises deploying the optical computing device as a pipeline or a downhole well tubular.

58. A method as defined in claim 53, wherein determining the characteristic of the fluid sample further comprises determining a presence of at least one of a C1-C6 hydrocarbon, salinity, sand content, pH, total dissolved solids, H2S, CO2, asphaltenes, waxes, saturates, resins or water.

59. An optical computing device to determine a characteristic of a fluid sample, the device comprising:
a device housing that attaches to a surface of a fluid-containing body;
an optical groove positioned on an exterior of the device housing along which a fluid sample may flow;
electromagnetic radiation that optically interacts with the fluid sample flowing along the optical groove to thereby produce sample-interacted light;
an optical element positioned inside the device housing to optically interact with the sample-interacted light to produce optically-interacted light which corresponds to the characteristic of the fluid sample; and
a detector positioned inside the device housing to measure the optically-interacted light and thereby generate a signal utilized to determine the characteristic of the fluid sample.

60. An optical computing device as defined in claim 59, wherein the device housing is dome-shaped.

61. An optical computing device as defined in claim 59, wherein the optical groove is an internal reflectance element.

62. An optical computing device as defined in claim 59, further comprising an electromagnetic radiation source positioned inside the device housing adjacent to the optical groove, the electromagnetic radiation source being adapted to generate the electromagnetic radiation, wherein the optical element is positioned adjacent to the optical groove such that the optical element receives the sample-interacted light emanating from the fluid sample.

63. An optical computing device as defined in claim 59, wherein the electromagnetic radiation source emits the electromagnetic radiation in a direction such that the electromagnetic radiation traverses an axis of the optical groove.

64. An optical computing device as defined in claim 59, wherein the optical groove has a "V" shape, a squared shape or a rounded shape.

65. An optical computing device as defined in claim 59, wherein the optical groove tapers into the device housing.

66. An optical computing device as defined in claim 59, further comprising multiple electromagnetic radiation sources and associated optical elements extending along the optical groove.

67. An optical computing device as defined in claim 59, further comprising a signal processor communicably coupled to the detector to computationally determine the characteristic of the fluid sample.

68. An optical computing device as defined in claim 59, wherein the optical element is an Integrated Computational Element.

69. An optical computing device as defined in claim 59, wherein the characteristic of the fluid sample is at least one of a C1-C6 hydrocarbon, salinity, sand content, pH, total dissolved solids, H2S, CO2, asphaltenes, waxes, saturates, resins or water.

70. An optical computing device as defined in claim 59, wherein the fluid-containing body is a pipeline or downhole well tubular.

71. An optical computing device as defined in claim 59, wherein the optical computing device is removably attached to the surface of the fluid-containing body.

72. A method utilizing an optical computing device to determine a characteristic of a fluid sample, the method comprising:
attaching the optical computing device to a surface of a fluid-containing body, the optical computing device comprising:
a device housing that attaches to the surface of the fluid-containing body; and
an optical groove positioned on an exterior of the device housing along which a fluid sample may flow;

optically interacting electromagnetic radiation with the fluid sample flowing along the optical groove to produce sample-interacted light;

optically interacting an optical element with the sample-interacted light to generate optically-interacted light which corresponds to a characteristic of the fluid sample;

generating a signal that corresponds to the optically-interacted light through utilization of a detector; and determining a characteristic of the fluid sample using the signal.

73. A method as defined in claim 72, wherein optically interacting electromagnetic radiation with the fluid sample further comprises conveying the electromagnetic radiation from an electromagnetic radiation source positioned inside the device housing adjacent to the optical groove, the electromagnetic radiation being conveyed in a direction such that the electromagnetic radiation traverses an axis of the optical groove.

74. A method as defined in claim 73, wherein optically interacting the optical element with the sample-interacted light further comprises conveying the sample-interacted light to the optical element positioned along the device housing adjacent to the optical groove opposite the electromagnetic radiation source.

75. A method as defined in claim 74, wherein attaching the optical computing device to the surface of the fluid-containing body further comprises attaching a plurality of optical computing devices to the surface of the fluid-containing body, the plurality of optical computing devices each comprising electromagnetic radiation sources and associated optical elements extending along the optical groove.

76. A method as defined in claim 72, wherein attaching the optical computing device to the surface of the fluid-containing body further comprises attaching at least one optical computing device to a surface of a pipeline or a downhole well tubular.

77. A method as defined in claim 72, wherein determining the characteristic of the fluid sample further comprises determining a presence of at least one of a C1-C6 hydrocarbon, salinity, sand content, pH, total dissolved solids, H2S, CO2, asphaltenes, waxes, saturates, resins or water.

* * * * *

UNITED STATES PATENT AND TRADEMARK OFFICE
CERTIFICATE OF CORRECTION

PATENT NO. : 9,459,244 B2  
APPLICATION NO. : 14/783349  
DATED : October 4, 2016  
INVENTOR(S) : Robert P. Freese et al.

Page 1 of 1

It is certified that error appears in the above-identified patent and that said Letters Patent is hereby corrected as shown below:

In the Specification

Column 8, Line 66: "PCT/US2013/04680" should read -- PCT/US2013/046810 --;
Column 11, Line 45: "PCT/US2013/4146877" should read -- PCT/US2013/046877 --.

Signed and Sealed this
Tenth Day of January, 2017

Michelle K. Lee
*Director of the United States Patent and Trademark Office*